United States Patent
McLuen et al.

(10) Patent No.: US 10,292,830 B2
(45) Date of Patent: *May 21, 2019

(54) BONE FUSION DEVICE, SYSTEM AND METHOD

(75) Inventors: Gary R. McLuen, Port Townsend, WA (US); Benjamin J. Remington, Modesto, CA (US); Daniel R. Baker, Seattle, WA (US); Joseph N. Logan, Trumbull, CT (US); Gregory C. Stalcup, Columbia City, IN (US); Daniel E. Gerbec, Logan, UT (US)

(73) Assignee: Neuropro Technologies, Inc., Modesto, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 13/571,254

(22) Filed: Aug. 9, 2012

(65) Prior Publication Data
US 2013/0204371 A1 Aug. 8, 2013

Related U.S. Application Data

(60) Provisional application No. 61/521,678, filed on Aug. 9, 2011.

(51) Int. Cl.
*A61F 2/44* (2006.01)
*A61F 2/28* (2006.01)
*A61F 2/30* (2006.01)

(52) U.S. Cl.
CPC ............ *A61F 2/4455* (2013.01); *A61F 2/442* (2013.01); *A61F 2/447* (2013.01); *A61F 2/4465* (2013.01);
(Continued)

(58) Field of Classification Search
CPC .......... A61F 2/44; A61F 2/442; A61F 2/4425; A61F 2/4455; A61F 2/446; A61F 2/4465;
(Continued)

(56) References Cited

U.S. PATENT DOCUMENTS 4,309,777 A 1/1982 Patil
4,767,040 A 8/1988 Miller et al.
(Continued)

FOREIGN PATENT DOCUMENTS

DE 29911382 U1 8/1999
JP 2274243 11/1990
(Continued)

OTHER PUBLICATIONS

Search Report from European Application No. EP13797446.
(Continued)

*Primary Examiner* — Kevin T Truong
*Assistant Examiner* — Tracy L Kamikawa
(74) *Attorney, Agent, or Firm* — Haverstock & Owens LLP

(57) ABSTRACT

A bone fusion method, system and device for insertion between bones that are to be fused together in order to replace degenerated discs and/or bones, for example, the vertebrae of a spinal column. The bone fusion device comprises a frame and one or more extendable plates that are able to be angled, rotatable, adjustable, and have top profiles designed to correct and/or match the replaced discs/bones. The bone fusion device is able to be inserted between or replace the vertebrae by using a minimally invasive procedure wherein the dimensions and/or other characteristics of the bone fusion device are selectable based on the type of minimally invasive procedure.

29 Claims, 23 Drawing Sheets

(52) U.S. Cl.
CPC ... *A61F 2/30965* (2013.01); *A61F 2002/2835* (2013.01); *A61F 2002/3008* (2013.01); *A61F 2002/3041* (2013.01); *A61F 2002/3052* (2013.01); *A61F 2002/3056* (2013.01); *A61F 2002/30232* (2013.01); *A61F 2002/30235* (2013.01); *A61F 2002/30265* (2013.01); *A61F 2002/30266* (2013.01); *A61F 2002/30365* (2013.01); *A61F 2002/30367* (2013.01); *A61F 2002/30372* (2013.01); *A61F 2002/30373* (2013.01); *A61F 2002/30397* (2013.01); *A61F 2002/30401* (2013.01); *A61F 2002/30403* (2013.01); *A61F 2002/30405* (2013.01); *A61F 2002/30411* (2013.01); *A61F 2002/30413* (2013.01); *A61F 2002/30415* (2013.01); *A61F 2002/30482* (2013.01); *A61F 2002/30484* (2013.01); *A61F 2002/30504* (2013.01); *A61F 2002/30507* (2013.01); *A61F 2002/30517* (2013.01); *A61F 2002/30522* (2013.01); *A61F 2002/30523* (2013.01); *A61F 2002/30528* (2013.01); *A61F 2002/30538* (2013.01); *A61F 2002/30556* (2013.01); *A61F 2002/30579* (2013.01); *A61F 2002/30588* (2013.01); *A61F 2002/30596* (2013.01); *A61F 2002/30598* (2013.01); *A61F 2002/30601* (2013.01); *A61F 2002/30604* (2013.01); *A61F 2002/30616* (2013.01); *A61F 2002/30777* (2013.01); *A61F 2002/30784* (2013.01); *A61F 2002/30827* (2013.01); *A61F 2002/30841* (2013.01); *A61F 2002/30843* (2013.01); *A61F 2002/30904* (2013.01); *A61F 2002/4475* (2013.01); *A61F 2002/4495* (2013.01); *A61F 2310/00359* (2013.01)

(58) Field of Classification Search
CPC .. A61F 2/447; A61F 2/4611; A61F 2002/443; A61F 2002/4475; A61F 2002/448; A61F 2002/4485
USPC ................................. 623/17.11, 17.15, 17.16
See application file for complete search history.

(56) References Cited

U.S. PATENT DOCUMENTS

| | | |
|---|---|---|
| 4,863,476 A | 9/1989 | Shepperd |
| 4,961,740 A | 10/1990 | Ray et al. |
| 5,015,247 A | 5/1991 | Michelson |
| 5,059,193 A | 10/1991 | Kuslich |
| 5,123,926 A | 6/1992 | Pisharodi |
| 5,171,278 A | 12/1992 | Pisharodi |
| 5,443,514 A | 8/1995 | Steffe |
| 5,458,642 A | 10/1995 | Beer et al. |
| 5,489,307 A | 2/1996 | Kuslich et al. |
| 5,522,899 A | 6/1996 | Michelson |
| 5,653,763 A | 8/1997 | Errico et al. |
| 5,658,335 A | 8/1997 | Allen |
| 5,665,122 A | 9/1997 | Kambin |
| 5,693,100 A | 12/1997 | Pisharodi |
| 5,702,391 A | 12/1997 | Lin |
| 5,716,415 A | 2/1998 | Steffee |
| 5,782,832 A * | 7/1998 | Larsen ............... A61F 2/30742 623/17.11 |
| 5,800,547 A | 9/1998 | Schafer et al. |
| 5,800,550 A | 9/1998 | Sertich |
| 5,827,328 A | 10/1998 | Buttermann |
| 5,865,848 A | 2/1999 | Baker |
| 5,885,287 A | 3/1999 | Bagby |
| 5,928,284 A | 7/1999 | Mehdizadeh |
| 5,980,522 A | 11/1999 | Koros et al. |
| 6,045,579 A | 4/2000 | Hochshuler et al. |
| 6,080,158 A | 6/2000 | Lin |
| 6,080,193 A | 6/2000 | Hochshuler et al. |
| 6,102,949 A | 8/2000 | Biedermann et al. |
| 6,102,950 A | 8/2000 | Vaccaro |
| 6,117,174 A | 9/2000 | Nolan |
| 6,129,763 A | 10/2000 | Chauvin et al. |
| 6,156,067 A | 12/2000 | Bryan et al. |
| 6,159,244 A | 12/2000 | Suddaby |
| 6,174,311 B1 | 1/2001 | Branch |
| 6,174,334 B1 | 1/2001 | Suddaby |
| 6,176,881 B1 | 1/2001 | Schar et al. |
| 6,176,882 B1 | 1/2001 | Biedermann et al. |
| 6,179,873 B1 | 1/2001 | Zientek |
| 6,183,517 B1 | 2/2001 | Suddaby |
| 6,190,414 B1 | 2/2001 | Young et al. |
| 6,231,609 B1 | 5/2001 | Mehdizadeh |
| 6,319,257 B1 | 11/2001 | Carignan et al. |
| 6,325,827 B1 | 12/2001 | Lin |
| 6,342,074 B1 | 1/2002 | Simpson |
| 6,371,968 B1 | 4/2002 | Kogasaka et al. |
| 6,371,987 B1 | 4/2002 | Weiland et al. |
| 6,375,655 B1 | 4/2002 | Zdeblick et al. |
| 6,375,683 B1 | 4/2002 | Crozet et al. |
| 6,409,766 B1 | 6/2002 | Brett |
| 6,419,705 B1 | 7/2002 | Erickson |
| 6,436,140 B1 | 8/2002 | Liu et al. |
| 6,443,989 B1 | 9/2002 | Jackson |
| 6,454,806 B1 | 9/2002 | Choen et al. |
| 6,454,807 B1 | 9/2002 | Jackson |
| 6,464,727 B1 | 10/2002 | Sharkey et al. |
| 6,488,710 B2 | 12/2002 | Besselink |
| 6,491,695 B1 | 12/2002 | Roggenbuck |
| 6,527,803 B1 | 3/2003 | Crozet et al. |
| 6,562,041 B1 | 5/2003 | Yonemura et al. |
| 6,572,619 B2 | 6/2003 | Santilli |
| 6,572,653 B1 | 6/2003 | Simonson |
| 6,575,042 B1 | 6/2003 | Rinner |
| 6,576,016 B1 | 6/2003 | Hochsuler et al. |
| 6,582,431 B1 | 6/2003 | Ray |
| 6,582,451 B1 | 6/2003 | Marucci |
| 6,582,467 B1 | 6/2003 | Teitelbaum et al. |
| 6,595,995 B2 | 7/2003 | Zdeblick et al. |
| 6,613,091 B1 | 9/2003 | Zdeblick et al. |
| 6,645,249 B2 | 11/2003 | Ralph et al. |
| 6,652,584 B2 | 11/2003 | Michelson |
| 6,666,888 B1 | 12/2003 | Jackson |
| 6,685,742 B1 | 2/2004 | Jackson |
| 6,706,070 B1 | 3/2004 | Wagner et al. |
| 6,709,458 B2 | 3/2004 | Michelson |
| 6,723,126 B1 | 4/2004 | Berry |
| 6,723,128 B2 | 4/2004 | Uk |
| 6,746,454 B2 | 6/2004 | Winterbottom et al. |
| 6,767,367 B1 | 7/2004 | Michelson |
| 6,770,095 B2 | 8/2004 | Grinberg et al. |
| 6,770,096 B2 | 8/2004 | Bolger et al. |
| 6,808,537 B2 | 10/2004 | Michelson |
| 6,821,298 B1 | 11/2004 | Jackson |
| 6,830,589 B2 | 12/2004 | Erickson |
| 6,835,206 B2 | 12/2004 | Jackson |
| 6,902,568 B2 | 6/2005 | Serhan |
| 6,923,830 B2 | 8/2005 | Michelson |
| 6,942,698 B1 | 9/2005 | Jackson |
| 6,962,606 B2 | 11/2005 | Michelson |
| 6,979,353 B2 | 12/2005 | Bresina |
| 6,989,011 B2 | 1/2006 | Paul et al. |
| 7,008,453 B1 | 3/2006 | Michelson |
| 7,018,415 B1 | 3/2006 | McKay |
| 7,041,309 B2 | 5/2006 | Remington et al. |
| 7,048,763 B2 | 5/2006 | Ralph et al. |
| 7,094,257 B2 | 8/2006 | Mujwid et al. |
| 7,097,648 B1 | 8/2006 | Globerman |
| 7,108,862 B2 | 9/2006 | Remington et al. |
| 7,118,598 B2 | 10/2006 | Michelson |
| 7,128,760 B2 | 10/2006 | Michelson |
| 7,166,130 B2 | 1/2007 | Ferre |
| 7,172,561 B2 | 2/2007 | Grimberg |
| 7,195,643 B2 | 3/2007 | Jackson |
| 7,211,112 B2 | 5/2007 | Baynham et al. |
| 7,217,291 B2 | 5/2007 | Zucherman et al. |

(56) References Cited

U.S. PATENT DOCUMENTS

| | | |
|---|---|---|
| 7,217,293 B2 | 5/2007 | Branch, Jr. |
| 7,220,280 B2 | 5/2007 | Kast et al. |
| 7,220,282 B2 | 5/2007 | Kuslich |
| 7,235,103 B2 | 6/2007 | Rivin |
| 7,238,186 B2 | 7/2007 | Zdeblick et al. |
| 7,323,011 B2 | 1/2008 | Shepard et al. |
| 7,331,994 B2 | 2/2008 | Gordon et al. |
| 7,331,996 B2 | 2/2008 | Sato et al. |
| 7,431,735 B2 | 10/2008 | Liu et al. |
| 7,445,636 B2 | 11/2008 | Michelson |
| 7,479,160 B2 | 1/2009 | Branch et al. |
| 7,500,992 B2 | 3/2009 | Li |
| 7,537,612 B2 | 5/2009 | Kunzler |
| 7,578,849 B2 | 8/2009 | Trieu |
| 7,584,682 B2 | 9/2009 | Hsiao |
| 7,588,573 B2 | 9/2009 | Berry |
| 7,608,107 B2 | 10/2009 | Michelson |
| 7,621,956 B2 | 11/2009 | Paul et al. |
| 7,674,296 B2 | 3/2010 | Rhoda et al. |
| 7,678,148 B2 | 3/2010 | Peterman |
| 7,682,376 B2 | 3/2010 | Trieu |
| 7,691,147 B2 | 4/2010 | Gutlin et al. |
| 7,703,727 B2 | 4/2010 | Selness |
| 7,727,280 B2 | 6/2010 | McLuen |
| 7,749,252 B2 | 7/2010 | Zucherman et al. |
| 7,753,958 B2 | 7/2010 | Gordon et al. |
| 7,758,617 B2 | 7/2010 | Lott et al. |
| 7,794,501 B2 | 9/2010 | Edie et al. |
| 7,799,081 B2 | 9/2010 | McKinley |
| D626,233 S | 10/2010 | Cipoletti et al. |
| 7,811,287 B2 | 10/2010 | Errico et al. |
| 7,811,327 B2 | 10/2010 | Hansell et al. |
| 7,828,849 B2 | 11/2010 | Lim |
| 7,837,688 B2 | 11/2010 | Boyer, II et al. |
| 7,837,734 B2 | 11/2010 | Zucherman et al. |
| 7,850,733 B2 | 12/2010 | Baynham et al. |
| 7,931,688 B2 | 4/2011 | Landry et al. |
| 7,932,825 B2 | 4/2011 | Berger |
| 7,935,117 B2 | 5/2011 | Sackett et al. |
| RE42,480 E | 6/2011 | Bryan et al. |
| 7,985,231 B2 | 7/2011 | Sankaran |
| 8,002,834 B2 | 8/2011 | de Villiers et al. |
| 8,043,295 B2 | 10/2011 | Reed |
| 8,062,375 B2 | 11/2011 | Glerum et al. |
| 8,070,813 B2 | 12/2011 | Grotz et al. |
| 8,105,382 B2 | 1/2012 | Olmos et al. |
| 8,110,004 B2 | 2/2012 | Valdevit et al. |
| 8,114,092 B2 | 2/2012 | Altarac |
| 8,187,332 B2 | 5/2012 | McLuen |
| 8,221,502 B2 | 7/2012 | Branch, Jr. |
| 8,262,666 B2 | 9/2012 | Baynham et al. |
| 8,262,736 B2 | 9/2012 | Michelson |
| 8,273,129 B2 | 9/2012 | Baynham et al. |
| 8,282,683 B2 | 10/2012 | McLaughlin et al. |
| 8,292,963 B2 | 10/2012 | Miller et al. |
| 8,303,601 B2 | 11/2012 | Bandeira et al. |
| 8,303,658 B2 | 11/2012 | Peterman |
| 8,308,801 B2 | 11/2012 | Halverson et al. |
| 8,308,804 B2 | 11/2012 | Krueger |
| 8,308,805 B2 | 11/2012 | Lynn |
| 8,317,025 B1 | 11/2012 | Kolozs et al. |
| 8,317,798 B2 | 11/2012 | Lim |
| 8,328,962 B2 | 12/2012 | Schussler |
| 8,337,562 B2 | 12/2012 | Landry et al. |
| 8,343,222 B2 | 1/2013 | Cope |
| 8,361,152 B2 | 1/2013 | McCormack et al. |
| 8,366,777 B2 | 2/2013 | Matthis et al. |
| 8,403,990 B2 | 3/2013 | Dryer et al. |
| 8,444,696 B2 | 5/2013 | Michelson |
| 8,444,697 B1 | 5/2013 | Butler et al. |
| 8,485,075 B1 | 7/2013 | Gauthier et al. |
| 8,579,904 B2 | 11/2013 | Siccardi |
| 8,585,763 B2 | 11/2013 | Olevsky et al. |
| 8,591,587 B2 | 11/2013 | Refai et al. |
| 8,597,360 B2 * | 12/2013 | McLuen et al. ............ 623/17.16 |
| 8,690,886 B2 | 4/2014 | Fedorov et al. |
| 8,734,337 B2 | 5/2014 | Deitch |
| 8,740,980 B2 | 6/2014 | Merves |
| 8,894,710 B2 | 11/2014 | Simpson et al. |
| 9,119,725 B2 | 9/2015 | Barrall |
| 9,216,098 B2 | 12/2015 | Trudeau |
| 9,308,098 B2 | 4/2016 | Boehm |
| 9,320,610 B2 | 4/2016 | Alheidt et al. |
| 9,358,672 B2 | 6/2016 | Gauthier et al. |
| 9,545,283 B2 | 1/2017 | Sack |
| 9,655,740 B1 | 5/2017 | Faulkner |
| 9,724,208 B2 | 8/2017 | Robinson |
| 9,737,316 B2 | 8/2017 | Bertagnoli |
| 9,750,617 B2 | 9/2017 | Lim |
| 9,757,111 B2 | 9/2017 | Fehling |
| 9,757,249 B2 | 9/2017 | Radcliffe |
| 9,757,250 B2 | 9/2017 | Josse |
| 9,782,267 B2 | 10/2017 | Barrall |
| 9,782,271 B2 | 10/2017 | Cipoletti |
| 9,801,734 B1 | 10/2017 | Stein |
| 9,931,224 B2 | 4/2018 | Lindenmann |
| 2002/0033305 A1 | 3/2002 | Koyama et al. |
| 2002/0128713 A1 | 9/2002 | Ferree |
| 2002/0128716 A1 | 9/2002 | Cohen et al. |
| 2002/0165613 A1 | 11/2002 | Lin et al. |
| 2003/0036762 A1 | 2/2003 | Kerr |
| 2003/0109932 A1 | 6/2003 | Keynan |
| 2003/0229355 A1 | 12/2003 | Keller |
| 2003/0236520 A1 | 12/2003 | Lim |
| 2004/0024461 A1 | 2/2004 | Ferree |
| 2004/0039448 A1 | 2/2004 | Pisharodi |
| 2004/0087947 A1 | 5/2004 | Lim et al. |
| 2004/0102774 A1 | 5/2004 | Trieu |
| 2004/0106998 A1 | 6/2004 | Ferree |
| 2004/0127993 A1 | 7/2004 | Kast et al. |
| 2004/0138750 A1 | 7/2004 | Michell |
| 2004/0148027 A1 | 7/2004 | Errico et al. |
| 2004/0153065 A1 | 8/2004 | Lim |
| 2004/0181285 A1 | 9/2004 | Simonson |
| 2004/0204762 A1 | 10/2004 | Ralph et al. |
| 2004/0230309 A1 | 11/2004 | DiMauro et al. |
| 2004/0243238 A1 | 12/2004 | Arnin et al. |
| 2005/0015149 A1 | 1/2005 | Michelson |
| 2005/0021042 A1 | 1/2005 | Marnay |
| 2005/0027360 A1 | 2/2005 | Webb et al. |
| 2005/0038515 A1 | 2/2005 | Kunzler |
| 2005/0065610 A1 | 3/2005 | Pisharodi |
| 2005/0107878 A1 | 5/2005 | Conchy |
| 2005/0182416 A1 | 8/2005 | Lim et al. |
| 2005/0278036 A1 | 12/2005 | Leonard et al. |
| 2005/0283236 A1 | 12/2005 | Razian |
| 2006/0052872 A1 | 3/2006 | Studer et al. |
| 2006/0069436 A1 | 3/2006 | Sutton |
| 2006/0074431 A1 | 4/2006 | Sutton |
| 2006/0095136 A1 | 5/2006 | McLuen |
| 2006/0116769 A1 | 6/2006 | Marnay et al. |
| 2006/0122701 A1 | 6/2006 | Kiester |
| 2006/0129244 A1 | 6/2006 | Ensign |
| 2006/0149381 A1 | 7/2006 | Kim |
| 2006/0155295 A1 | 7/2006 | Supper |
| 2006/0190084 A1 | 8/2006 | Doubler et al. |
| 2006/0200243 A1 | 9/2006 | Rothman et al. |
| 2006/0200244 A1 | 9/2006 | Assaker |
| 2006/0235426 A1 | 10/2006 | Lim |
| 2006/0241643 A1 | 10/2006 | Lim et al. |
| 2006/0241764 A1 | 10/2006 | Michelson |
| 2006/0241766 A1 | 10/2006 | Felton et al. |
| 2006/0241767 A1 | 10/2006 | Doty |
| 2006/0241770 A1 | 10/2006 | Rhoda et al. |
| 2006/0241774 A1 | 10/2006 | Attali et al. |
| 2006/0247679 A1 | 11/2006 | Peterman |
| 2006/0253201 A1* | 11/2006 | McLuen ............... A61F 2/4455 623/17.15 |
| 2006/0276899 A1 | 12/2006 | Zipnick et al. |
| 2006/0293752 A1 | 12/2006 | Moumene et al. |
| 2006/0293753 A1 | 12/2006 | Thramann |
| 2007/0050030 A1 | 3/2007 | Kim |
| 2007/0067038 A1 | 3/2007 | Studer et al. |
| 2007/0093897 A1 | 4/2007 | Gerbec et al. |

(56) References Cited

U.S. PATENT DOCUMENTS

| | | |
|---|---|---|
| 2007/0093901 A1 | 4/2007 | Grotz et al. |
| 2007/0191954 A1 | 8/2007 | Hansell et al. |
| 2007/0209222 A1 | 9/2007 | Fischer |
| 2007/0213641 A1 | 9/2007 | Francis |
| 2007/0233254 A1 | 10/2007 | Grotz et al. |
| 2007/0255407 A1 | 11/2007 | Castleman et al. |
| 2007/0255413 A1 | 11/2007 | Edie |
| 2007/0255415 A1 | 11/2007 | Edie et al. |
| 2007/0260260 A1 | 11/2007 | Hahn |
| 2007/0270954 A1 | 11/2007 | Wu |
| 2007/0270968 A1* | 11/2007 | Baynham ............... A61F 2/447 623/17.11 |
| 2007/0282372 A1 | 12/2007 | Yedlicka |
| 2007/0282441 A1 | 12/2007 | Stream et al. |
| 2008/0009868 A1 | 1/2008 | Gotfried et al. |
| 2008/0009880 A1 | 1/2008 | Warnick et al. |
| 2008/0015701 A1 | 1/2008 | Garcia et al. |
| 2008/0021555 A1 | 1/2008 | White |
| 2008/0021558 A1 | 1/2008 | Thramann |
| 2008/0021559 A1 | 1/2008 | Thramann |
| 2008/0046083 A1 | 2/2008 | Hewko |
| 2008/0051902 A1 | 2/2008 | Dwyer |
| 2008/0077153 A1 | 3/2008 | Pernsteiner et al. |
| 2008/0097435 A1 | 4/2008 | Deridder et al. |
| 2008/0114367 A1 | 5/2008 | Meyer |
| 2008/0125778 A1 | 5/2008 | Li |
| 2008/0132949 A1 | 6/2008 | Aferzon et al. |
| 2008/0140207 A1* | 6/2008 | Olmos et al. ............... 623/17.16 |
| 2008/0147193 A1* | 6/2008 | Matthis et al. ............ 623/17.16 |
| 2008/0154381 A1 | 6/2008 | Parrish |
| 2008/0161817 A1 | 7/2008 | Parsons et al. |
| 2008/0177275 A1 | 7/2008 | Wing et al. |
| 2008/0183293 A1 | 7/2008 | Parry et al. |
| 2008/0208264 A1 | 8/2008 | Lazarof |
| 2008/0243125 A1 | 10/2008 | Guzman et al. |
| 2008/0269756 A1 | 10/2008 | Tomko |
| 2008/0269905 A1 | 10/2008 | Link |
| 2008/0287995 A1 | 11/2008 | Gauthier |
| 2008/0288073 A1 | 11/2008 | Renganath |
| 2008/0288076 A1 | 11/2008 | Soo et al. |
| 2008/0306489 A1 | 12/2008 | Altarac et al. |
| 2009/0030422 A1 | 1/2009 | Parsons et al. |
| 2009/0099601 A1 | 4/2009 | Aferzon et al. |
| 2009/0105828 A1 | 4/2009 | Gimbel |
| 2009/0112217 A1 | 4/2009 | Hester |
| 2009/0112220 A1 | 4/2009 | Kraus |
| 2009/0164018 A1 | 6/2009 | Sommerich |
| 2009/0164020 A1 | 6/2009 | Janowski et al. |
| 2009/0182343 A1 | 7/2009 | Trudeau et al. |
| 2009/0198241 A1 | 8/2009 | Phan |
| 2009/0198245 A1 | 8/2009 | Phan |
| 2009/0198338 A1 | 8/2009 | Phan |
| 2009/0210061 A1 | 8/2009 | Sledge |
| 2009/0222100 A1 | 9/2009 | Cipoletti et al. |
| 2009/0222101 A1 | 9/2009 | de Villiers et al. |
| 2009/0228110 A1 | 9/2009 | McClintock |
| 2009/0265008 A1 | 10/2009 | Thibodeau |
| 2009/0292361 A1 | 11/2009 | Lopez |
| 2009/0299478 A1 | 12/2009 | Carls et al. |
| 2009/0306672 A1 | 12/2009 | Reindel et al. |
| 2010/0010494 A1 | 1/2010 | Quirno |
| 2010/0023057 A1 | 1/2010 | Aeschlimann et al. |
| 2010/0024487 A1 | 2/2010 | Khoo et al. |
| 2010/0042219 A1 | 2/2010 | Antonacci et al. |
| 2010/0057204 A1 | 3/2010 | Kadaba et al. |
| 2010/0100100 A1 | 4/2010 | Refai |
| 2010/0114106 A1 | 5/2010 | Weber |
| 2010/0114183 A1 | 5/2010 | Wassinger et al. |
| 2010/0145456 A1 | 6/2010 | Simpson et al. |
| 2010/0168862 A1 | 7/2010 | Edie |
| 2010/0204795 A1 | 8/2010 | Greenhalgh |
| 2010/0211119 A1 | 8/2010 | Refai |
| 2010/0211176 A1 | 8/2010 | Greenhalgh |
| 2010/0222884 A1 | 9/2010 | Greenhalgh |
| 2010/0234956 A1 | 9/2010 | Attia et al. |
| 2010/0241231 A1 | 9/2010 | Marino et al. |
| 2010/0256768 A1 | 10/2010 | Lim et al. |
| 2010/0262247 A1 | 10/2010 | Arnin |
| 2010/0280622 A1 | 11/2010 | McKinley |
| 2010/0286779 A1 | 11/2010 | Thibodeau |
| 2010/0286780 A1 | 11/2010 | Dyer et al. |
| 2010/0292796 A1 | 11/2010 | Greenhalgh et al. |
| 2010/0298939 A1 | 11/2010 | Defosse et al. |
| 2010/0324606 A1 | 12/2010 | Moskowitz et al. |
| 2011/0015638 A1 | 1/2011 | Pischl et al. |
| 2011/0015741 A1 | 1/2011 | Melkent |
| 2011/0015742 A1 | 1/2011 | Hong |
| 2011/0015747 A1 | 1/2011 | McManus et al. |
| 2011/0035011 A1 | 2/2011 | Cain |
| 2011/0054621 A1 | 3/2011 | Lim |
| 2011/0077738 A1 | 3/2011 | Ciupik et al. |
| 2011/0087329 A1 | 4/2011 | Poulos |
| 2011/0112587 A1 | 5/2011 | Patel et al. |
| 2011/0130835 A1 | 6/2011 | Ashley et al. |
| 2011/0130838 A1 | 6/2011 | Morgenstern Lopez |
| 2011/0138948 A1 | 6/2011 | Jimenez et al. |
| 2011/0160861 A1 | 6/2011 | Jimenez |
| 2011/0172716 A1 | 7/2011 | Glerum |
| 2011/0172774 A1 | 7/2011 | Varela |
| 2011/0202135 A1 | 8/2011 | Baek |
| 2011/0213465 A1 | 9/2011 | Landry et al. |
| 2011/0218627 A1 | 9/2011 | Rampersaud et al. |
| 2011/0230970 A1* | 9/2011 | Lynn et al. ............... 623/17.16 |
| 2011/0238184 A1 | 9/2011 | Zdeblick et al. |
| 2011/0251692 A1 | 10/2011 | McLaughlin |
| 2011/0282453 A1* | 11/2011 | Greenhalgh et al. ...... 623/17.16 |
| 2011/0301712 A1 | 12/2011 | Palmatier et al. |
| 2011/0307066 A1 | 12/2011 | Lim et al. |
| 2011/0319997 A1 | 12/2011 | Glerum |
| 2012/0035729 A1 | 2/2012 | Glerum et al. |
| 2012/0058451 A1 | 3/2012 | Lazarof |
| 2012/0059470 A1 | 3/2012 | Weiman |
| 2012/0059472 A1 | 3/2012 | Weiman |
| 2012/0059473 A1 | 3/2012 | Weiman |
| 2012/0059474 A1 | 3/2012 | Weiman |
| 2012/0059475 A1 | 3/2012 | Weiman |
| 2012/0059481 A1 | 3/2012 | Abernathie et al. |
| 2012/0064487 A1 | 3/2012 | Lazarof |
| 2012/0064488 A1 | 3/2012 | Lazarof |
| 2012/0071979 A1 | 3/2012 | Zipnick |
| 2012/0089228 A1 | 4/2012 | Poulos |
| 2012/0130494 A1 | 5/2012 | DeLurio et al. |
| 2012/0136448 A1 | 5/2012 | Seifert et al. |
| 2012/0143194 A1 | 6/2012 | Seifert et al. |
| 2012/0143201 A1 | 6/2012 | Seifert et al. |
| 2012/0150304 A1 | 6/2012 | Glerum et al. |
| 2012/0150305 A1 | 6/2012 | Glerum et al. |
| 2012/0158071 A1 | 6/2012 | Jimenez |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0191194 A1 | 7/2012 | Olmos et al. |
| 2012/0197403 A1 | 8/2012 | Merves |
| 2012/0197404 A1 | 8/2012 | Brun et al. |
| 2012/0203347 A1 | 8/2012 | Glerum et al. |
| 2012/0209384 A1 | 8/2012 | Arnold et al. |
| 2012/0209386 A1 | 8/2012 | Triplett |
| 2012/0226357 A1 | 9/2012 | Varela |
| 2012/0232552 A1 | 9/2012 | Morgenstern Lopez |
| 2012/0232601 A1 | 9/2012 | Chabansky et al. |
| 2012/0232659 A1 | 9/2012 | Himmelberger |
| 2012/0232660 A1 | 9/2012 | Davenport |
| 2012/0245691 A1 | 9/2012 | Reimels |
| 2012/0253412 A1 | 10/2012 | Lee |
| 2012/0271422 A1 | 10/2012 | Miller et al. |
| 2012/0277810 A1 | 11/2012 | Siccardi et al. |
| 2012/0277875 A1 | 11/2012 | Arnin |
| 2012/0290090 A1 | 11/2012 | Glerum et al. |
| 2012/0303124 A1 | 11/2012 | McLuen et al. |
| 2012/0310350 A1 | 12/2012 | Farris et al. |
| 2012/0323327 A1 | 12/2012 | McAfee |
| 2012/0323328 A1 | 12/2012 | Weiman |
| 2012/0330421 A1 | 12/2012 | Weiman |
| 2012/0330422 A1 | 12/2012 | Weiman |

(56) References Cited

U.S. PATENT DOCUMENTS

| | | |
|---|---|---|
| 2013/0006359 A1 | 1/2013 | Fedorov |
| 2013/0006361 A1 | 1/2013 | Glerum et al. |
| 2013/0006364 A1 | 1/2013 | McCormack et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0023993 A1 | 1/2013 | Weiman |
| 2013/0023994 A1 | 1/2013 | Glerum |
| 2013/0030534 A1 | 1/2013 | DeLurio et al. |
| 2013/0035724 A1 | 2/2013 | Fitzpatrick |
| 2013/0035763 A1 | 2/2013 | Krueger |
| 2013/0053962 A1 | 2/2013 | Moskowitz et al. |
| 2013/0085572 A1 | 4/2013 | Glerum et al. |
| 2013/0103153 A1 | 4/2013 | Blackwell et al. |
| 2013/0103156 A1 | 4/2013 | Packer et al. |
| 2013/0110248 A1 | 5/2013 | Zipnick |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197642 A1 | 8/2013 | Ernst |
| 2013/0204371 A1 | 8/2013 | McLuen et al. |
| 2013/0211525 A1 | 8/2013 | McLuen et al. |
| 2013/0253650 A1 | 9/2013 | Ashley |
| 2013/0274883 A1 | 10/2013 | McLuen et al. |
| 2013/0310938 A1 | 11/2013 | Sournac et al. |
| 2014/0012383 A1 | 1/2014 | Triplett |
| 2014/0066941 A1 | 3/2014 | Mignucci |
| 2014/0088708 A1 | 3/2014 | McLaughlin et al. |
| 2014/0121774 A1 | 5/2014 | Glerum |
| 2014/0148902 A1 | 5/2014 | Dickson |
| 2014/0156006 A1 | 6/2014 | Bannigan |
| 2014/0156008 A1 | 6/2014 | Flickinger et al. |
| 2014/0236296 A1 | 8/2014 | Wagner et al. |
| 2014/0249629 A1 | 9/2014 | Moskowitz et al. |
| 2014/0257485 A1 | 9/2014 | Matthis et al. |
| 2014/0277470 A1 | 9/2014 | Baynham |
| 2014/0277490 A1 | 9/2014 | Perloff |
| 2014/0277500 A1 | 9/2014 | Logan et al. |
| 2014/0277504 A1 | 9/2014 | Forton et al. |
| 2014/0277509 A1 | 9/2014 | Robinson |
| 2014/0277510 A1 | 9/2014 | Robinson |
| 2014/0288652 A1 | 9/2014 | Boehm et al. |
| 2014/0316522 A1 | 10/2014 | Weiman et al. |
| 2014/0343677 A1 | 11/2014 | Davis et al. |
| 2014/0343678 A1 | 11/2014 | Suddaby et al. |
| 2015/0018954 A1 | 1/2015 | Loebl |
| 2015/0094815 A1 | 4/2015 | Emerick et al. |
| 2015/0238327 A1 | 8/2015 | Cheng |
| 2015/0250606 A1 | 9/2015 | McLean |
| 2015/0250609 A1 | 9/2015 | McLean |
| 2015/0282797 A1 | 10/2015 | O'Neil et al. |
| 2015/0374509 A1 | 12/2015 | McLean |
| 2016/0106551 A1 | 4/2016 | Grimberg, Jr. |
| 2016/0256291 A1 | 9/2016 | Miller |
| 2016/0354211 A1 | 12/2016 | Packer |
| 2017/0071753 A1 | 3/2017 | Josse |
| 2017/0100260 A1 | 4/2017 | Duffield |
| 2017/0119542 A1 | 5/2017 | Logan et al. |
| 2017/0224500 A1 | 8/2017 | Perloff |
| 2017/0245997 A1 | 8/2017 | Trischler |
| 2017/0273804 A1 | 9/2017 | Emerick |
| 2017/0304066 A1 | 10/2017 | Smith |
| 2017/0325969 A1 | 11/2017 | McLean |
| 2018/0049890 A1 | 2/2018 | Propejoy |

FOREIGN PATENT DOCUMENTS

| | | |
|---|---|---|
| WO | WO9117723 | 11/1991 |
| WO | 2006134262 A1 | 12/2006 |
| WO | 2008035849 A1 | 3/2008 |
| WO | 2008070863 A2 | 6/2008 |
| WO | 2008086276 A2 | 7/2008 |
| WO | 2010006258 | 1/2010 |
| WO | 2010045301 A1 | 4/2010 |
| WO | 2010121030 A2 | 10/2010 |
| WO | 2011116136 A1 | 9/2011 |
| WO | 2013023096 A1 | 2/2013 |
| WO | 2013023098 A1 | 2/2013 |
| WO | 2013025876 A1 | 2/2013 |

OTHER PUBLICATIONS

International Search Report and Written Opinion from International Application No. PCT/US2018/013394.

International Search Report and Written Opinion from International Application No. PCT/US18/13681.

International Search Report and Written Opinion from International Application No. PCT/US18/13644.

International Search Report and Written Opinion from International Application No. PCT/US18/13715.

Australian Examination Report No. 1, from Australian Patent Application No. 2014236698.

International Search Report and Written Opinion from International Application No. PCT/US2018/013717 dated Mar. 7, 2018.

International Search Report and Written Opinion from International Application No. PCT/US2018/013851 dated May 17, 2018.

\* cited by examiner

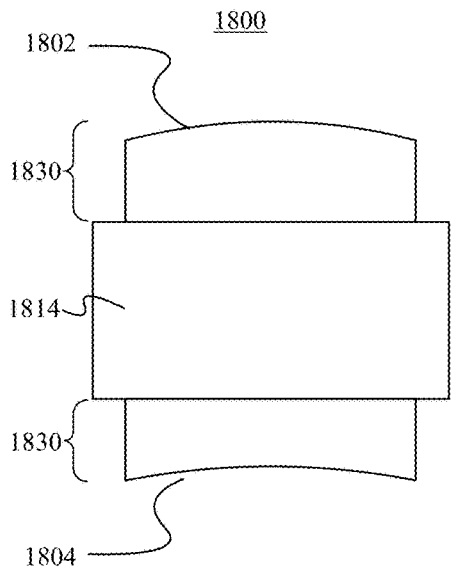
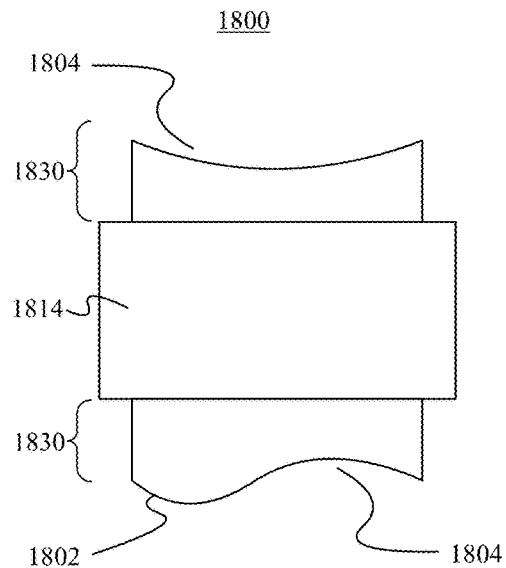
Fig. 18A  Fig. 18B
A user selects the tabs of a bone fusion device based on the shape of the top surface of the tabs and the shape of the surfaces to which the tabs are to be fused. ~1902
The user inserts the bone fusion device with the selected tabs in between the desired bones. ~1904
Fig. 19

BONE FUSION DEVICE, SYSTEM AND METHOD

RELATED APPLICATIONS

This application claims priority under 35 U.S.C. § 119(e) of U.S. Provisional Patent Application Ser. No. 61/521,678, filed Aug. 9, 2011, and entitled "BONE FUSION DEVICE, SYSTEM AND METHOD," which is hereby incorporated by reference.

FIELD OF THE INVENTION

This invention relates generally to bone fusion devices. More specifically, the present invention relates to devices for fusing vertebrae of the spine or other bones.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. Similarly, vertebrae are able to weaken due to impact or disease reducing their ability to properly distribute forces on the spine. As a result, nerves may become pinched, causing pain that radiates into other parts of the body, or instability of the vertebrae may ensue.

One method for correcting disc and/or vertebrae-related disorders is to insert a fusion cage as a replacement for and/or in between the vertebrae to act as a structural replacement for the deteriorated disc and/or vertebrae. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit. However, it is difficult to retain this bone graft material in the cage and in the proper positions to stimulate bone growth.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present invention is a bone fusion method, system and device for insertion between bones that are to be fused together in order to replace degenerated discs and/or bones, for example, the vertebrae of a spinal column. The bone fusion device comprises a frame and one or more extendable plates that are able to be angled, rotatable, adjustable, and have top profiles designed to correct and/or match the replaced discs/bones. The bone fusion device is able to be inserted between or replace the vertebrae by using minimally invasive procedure wherein the dimensions and/or other characteristics of the bone fusion device are selectable based on the type of minimally invasive procedure. The bone fusion device of some embodiments is filled and/or surrounded with bone graft material, wherein the bone graft material is maintained in desired shapes and locations in relation to the bones with one or more mesh bags. In some embodiments, one or more of the bone fusion devices are able to be coupled together and/or with a bone replacement body. As a result, the bone fusion device, system and method is able to customized to the needs of the surgeon and patient thereby increasing the effectiveness and safety of the bone fusion procedures.

A first aspect of the present application is directed to a bone fusion device for insertion into a desired location. The bone fusion device comprises a body having a first end and an interior cavity, one or more tabs each having a support rib, wherein the tabs are configured to selectively move from a retracted position within the body to an extended position extending out of the body and one or more extending blocks configured to slide within the body in order to move the tabs between the retracted position and the extended position, wherein the extending blocks each have a rib slot and are positioned adjacent to the tabs within the interior cavity such that each support rib slides within one or more of the rib slots when the tabs move between the retracted position and the extended position. In some embodiments, the outward facing surface of the tabs comprise a plurality of teeth such that the outward facing surface is serrated. In some embodiments, the body comprises an exterior surface having one or more surface channels. In some embodiments, each of the surface channels comprise a gripping aperture for receiving a fingertip of a finger of a gripping apparatus positioned within the surface channels. In some embodiments, the device further comprises a positioning element having a positioning aperture and mechanically coupled with the extending blocks such that moving the positioning element causes the extending blocks to slide within the body. In some embodiments, the surface channels are positioned along the exterior surface on a plane perpendicular to the aperture of the positioning element such that the fingers of the gripping apparatus are able to enter the one or more surface channels by moving parallel to the plane. In some embodiments, the body of the bone fusion device has a height of less than or equal to 5 mm. In some embodiments, the bone fusion device consists of a single tab. In some embodiments, the body has a top view profile selected from the group consisting of oval, kidney shaped, round and banana shaped. In some embodiments, one or more of the tabs have a top view profile selected from the group consisting of oval, kidney shaped, round and banana shaped. In some embodiments, the tabs have a top view profile with the same shape as the top view profile of the body. In some embodiments, the positioning aperture of an angled portion of the positioning element is accessible from exterior to the body at an angle non-parallel with the direction of motion of the extending blocks. In some embodiments, the outward facing surface of the tabs is non-planar. In some embodiments, the outward facing surface of the tabs is convex or concave. In some embodiments, the plane of the outward facing surface of the tabs is angled with respect to the plane of the bottom of the tabs. In some embodiments, the tabs are modular and detachably coupled to the body such that a tab is able to be selectively removed and replaced by another tab. In some embodiments, the tabs are rotatable with respect to the body. In some embodiments, the device further comprises one or more bone graft bags coupled to the body for holding bone graft material. In some embodiments, the bone graft bags are coupled to the exterior of the body. In some embodiments, the bone graft bags are positioned within the interior cavity. In some embodiments, the bone graft bags comprise a mesh frame having one or more support bars such that the bone graft bags are not flaccid. In some embodiments, the bone graft bags comprise one or more openings for inserting bone graft material and a bag fastener configured to close the opening. In some embodiments, the bone graft bags have a cylindrical shape.

A second aspect of the present application is directed to a method of implanting a bone fusion device into a desired location. The method comprises inserting the bone fusion device in the desired location, wherein the bone fusion device comprises a body having an interior cavity that houses one or more tabs each having an inner surface and a support rib, and one or more extending blocks each having a rib slot and extending the one or more tabs from a retracted position within the interior cavity to an extended position at least partially outside the interior cavity by moving at least one of the plurality of extending blocks along the inner surface of the tabs such that the rib slots slide along the support ribs positioned at least partially within the ribs slots. In some embodiments, the method further comprises retracting the tabs of the bone fusion device into the retracted position before inserting the bone fusion device into the desired location. In some embodiments, moving the extending blocks comprises manipulating a positioning element of the bone fusion device coupled with the extending blocks and having a positioning aperture. In some embodiments, the method further comprises securing a gripping apparatus to the bone fusion device by inserting one or more fingers of the gripping apparatus into one or more channels on the exterior surface of the body of the bone fusion device. In some embodiments, the method further comprises securing the fingers within the channels by inserting one or more fingertips of the fingers into one or more apertures of the channels. In some embodiments, the channels are positioned along the exterior surface on a plane perpendicular to the positioning aperture such that the fingers of the gripping apparatus are able to enter the channels by moving parallel to the plane. In some embodiments, an outward facing surface of the tabs comprises a plurality of teeth such that the outward facing surface is serrated. In some embodiments, the method further comprises selecting a bone fusion device having a body with a top view profile that substantially matches the cross-sectional profile of the bones from a plurality of bone fusion devices having bodies with different top view profiles. In some embodiments, the method further comprises selecting a bone fusion device having tabs with a top view profile that substantially matches the cross-sectional profile of the bones from a plurality of bone fusion devices having tabs with different top view profiles. In some embodiments, the method further comprises selecting a bone fusion device having an angled portion of the positioning element with a positioning aperture that is accessible from exterior to the body at an angle that substantially matches the angle of attack of the type of surgery. In some embodiments, the insertion the bone fusion device is at an angle corresponding to a type of surgeries are selected from the group consisting of anterior, posterior, lateral, far-lateral, extra-lateral, extreme-lateral and transforminal. In some embodiments, the method further comprises selecting one or more tabs having a non-planar outward facing surface that substantially corresponds to the surface of the bones to be contacted from a plurality of tabs with different non-planar outward facing surfaces. In some embodiments, the method further comprises selecting one or more tabs with outward facing surfaces having planes with respect to the plane of the bottom of the tabs that correspond to the angle of the plane of the surface of the bones to be contacted from a plurality of tabs with outward facing surfaces having planes of different angles with respect to the plane of the bottom of the tabs. In some embodiments, the method further comprises replacing one or more of the tabs of the bone fusion device with one or more replacement tabs. In some embodiments, the method further comprises rotating the tabs in the extended position until the tabs are at a desired angle with respect to the body. In some embodiments, the method further comprises inserting bone graft material into the bone graft bags through the openings and then closing the openings with the bag fastener. In some embodiments, the method further comprises coupling the bone graft bags to the body.

A third aspect of the present application is directed to a bone fusion system for insertion into a desired location. The system comprises one or more bone fusion devices each comprising a body having an interior cavity and one or more tabs having one or more device fasteners, wherein the tabs are configured to selectively extend from a retracted position within the interior cavity to an extended position at least partially outside of the interior cavity and one or more spacers having one or more spacer fasteners, wherein the spacer fasteners are configured to detachably couple to the device fasteners in order to couple the one or more bone fusion devices to the one or more spacers. In some embodiments, the one or more spacers are hollow. In some embodiments, the device fasteners are configured to detachably couple to other device fasteners in order to couple two or more bone fusion devices together. In some embodiments, the spacer fasteners are configured to detachably couple to other spacer fasteners in order to couple two or more spacers together. In some embodiments, the spacer fasteners and the device fasteners comprise one or more rails and one or more slats, wherein the slats are configured to slid under the one or more rails in order to detachably couple the spacer fasteners and the device fasteners together. In some embodiments, the one or more slats and one or more rails comprise one or more snap-fit members and one or more cutouts, wherein the snap-fit members are configured to depress when the slats are slid under the rails and spring into the one or more cutouts when aligned with the one or more cutouts in order to prevent the slats from sliding out from under the rails. In some embodiments, the body comprises one or more device fasteners.

A fourth aspect of the present application is directed to a bone fusion device for insertion into a desired location. The device comprises a body having an interior cavity and one or more tabs having one or more device fasteners, wherein the tabs are configured to selectively extend from a retracted position within the interior cavity to an extended position at least partially outside of the interior cavity, and further wherein the device fasteners are configured to detachably couple to each other in order to couple the bone fusion device to other bone fusion devices. In some embodiments, the body comprises one or more device fasteners configured to detachably couple to other device fasteners in order to couple the body of the bone fusion device to other bone fusion devices. In some embodiments, the device fasteners comprise one or more rails and one or more slats, wherein the slats are configured to slid under the one or more rails in order to detachably couple the device fasteners together. In some embodiments, the one or more slats and one or more rails comprise one or more snap-fit members and one or more cutouts, wherein the snap-fit members are configured to depress when the slats are slid under the rails and spring into the one or more cutouts when aligned with the one or more cutouts in order to prevent the slats from sliding out from under the rails.

Another aspect of the present application is directed to a method of implanting a bone fusion apparatus into a desired location having a height. The method comprises detachably coupling together two or more of the group consisting of bone fusion devices having a body and one or more extendable tabs and spacers to form a bone fusion assembly, inserting the bone fusion assembly into the desired location and extending one or more of the tabs out from the bodies to extended positions such that the height of the bone fusion assembly is substantially similar to the height of the desired location. In some embodiments, the number of spacers and bone fusion devices coupled together is based on the height of the desired location. In some embodiments, the one or more spacers are hollow. In some embodiments, the detachably coupling comprises coupling one of the bone fusion devices to another of the bone fusion device. In some embodiments, the detachably coupling comprises coupling one of the spacers to another of the spacers. In some embodiments, the detachably coupling comprises coupling one of the spacers to one or more of the bone fusion devices. In some embodiments, the bone fusion devices and spacers comprise one or more rails and one or more slats and the detachably coupling comprises sliding the slats under the rails. In some embodiments, the one or more slats and one or more rails comprise one or more snap-fit members and one or more cutouts and the detachably coupling comprises depressing the snap-fit members when the slats are slid under the rails and springing the snap-fit members into the one or more cutouts when the snap-fit members are aligned with one or more of the cutouts in order to prevent the slats from sliding out from under the rails.

Another aspect of the present application is directed to a bone fusion device for insertion into a desired location. The bone fusion device comprises a body having an interior cavity, one or more tabs having an outward facing surface and configured to selectively move between a retracted position within the interior cavity and an extended position extending out of the body in order to brace the bone fusion device in the desired location and a tab positioning assembly coupled with the one or more tabs within the interior cavity, the tab positioning assembly having an extension positioning element configured to move the tabs between the retracted position and the extended position and an angle positioning element configured to change the angle of the outward facing surface with respect to the body. In some embodiments, the tab positioning assembly is configured to enable the position of the tabs between the retracted position and the extended position and the angle of the outward facing surface with respect to the body to be adjusted independently. In some embodiments, the tab positioning assembly is configured to enable the position of the tabs between the retracted position and the extended position and the angle of the outward facing surface with respect to the body to be adjusted simultaneously.

Another aspect of the present application is directed to a method of implanting a bone fusion apparatus into a desired location. The method comprises inserting the bone fusion device into the desired location, wherein the bone fusion device comprises a body having an interior cavity, one or more extendable tabs having an outward facing surface and a tab positioning assembly coupled with the one or more tabs, moving the tabs between a retracted position within the interior cavity and an extended position extending out of the cavity with an extension positioning element of the tab positioning assembly and adjusting the angle of the outward facing surface with respect to the body with an angle positioning element of the tab positioning assembly. In some embodiments, the movement of the tabs between the retracted position and the extended position is independent of the adjustment of the angle of the outward facing surface with respect to the body. In some embodiments, the movement of the tabs between the retracted position and the extended position and the adjustment of the angle of the outward facing surface with respect to the body occur simultaneously.

Yet another aspect of the present application is directed to a bone fusion assembly for insertion into a desired location. The bone fusion assembly comprises a body having a front end, a back end, an interior cavity, an exterior surface and one or more canals positioned along the exterior surface, one or more hollow members positioned at least partially within the canals, one or more tabs configured to selectively move between a retracted position within the interior cavity and an extended position extending out of the body in order to brace the bone fusion device in the desired location, a positioning element positioned within the interior cavity and accessible from exterior to the body through the front end and a plurality of extending blocks coupled with the positioning element and in contact with the one or more tabs such that moving the positioning element causes the extending blocks to move the one or more tabs between the extended position and the retracted position. In some embodiments, the canals are accessible from the front end and extend through the a plane perpendicular to the front end. In some embodiments, the canals extend from the exterior surface to the interior cavity. In some embodiments, the hollow members comprise one or more apertures and are filled with bone grafting material. In some embodiments, at least one of the hollow members is curved and extends from within one of the canals into the interior cavity of the body.

BRIEF DESCRIPTION OF THE DRAWINGS

FIG. 18A illustrates a side profile view of a bone fusion device according to some embodiments.

FIG. 18B illustrates a side profile view of a bone fusion device according to some embodiments.

FIG. 19 illustrates a flowchart directed to a method of using the bone fusion device according to some embodiments.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1A:
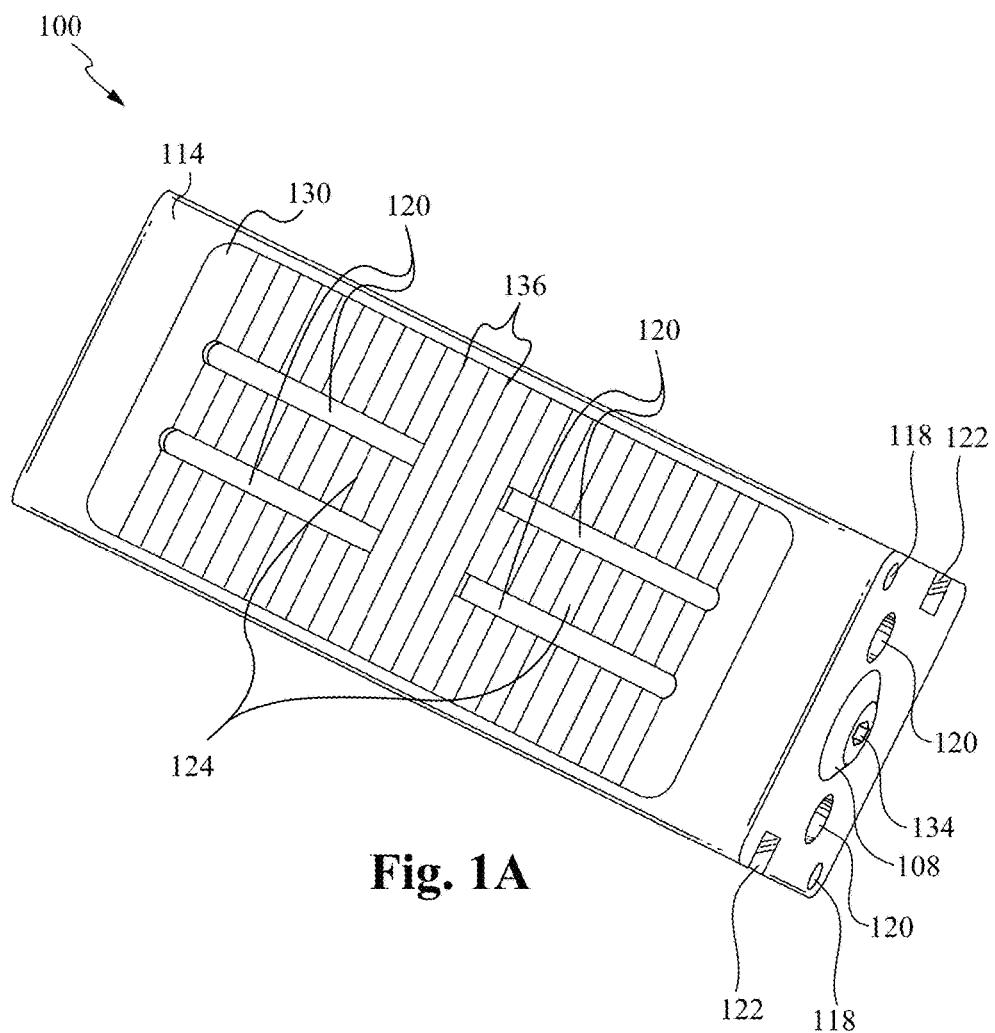
FIG. 1A illustrates a top perspective view of the bone fusion device according to some embodiments.
Figure 1B:
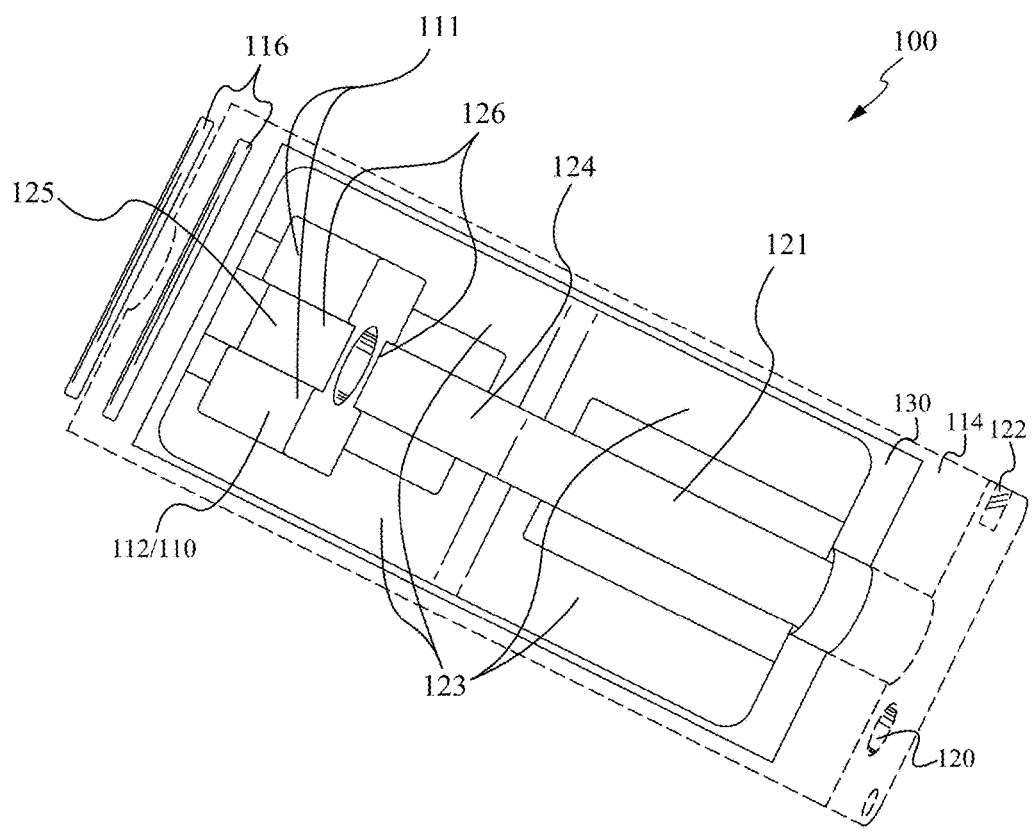
FIG. 1B illustrates a top cutout view of the bone fusion device according to some embodiments.

FIGS. 1A and 1B illustrate a top perspective and cutout view of the bone fusion device 100 according to some embodiments. As shown, the bone fusion device 100 has a substantially rectangular shape and has two end faces. The bone fusion device 100 is able to be constructed from a high strength biocompatible material, such as titanium, which has the strength to withstand forces in the spine that are generated by a patient's body weight and daily movements. Alternatively, part of all of the bone fusion device 100 is able to be constructed from one or more of the group consisting of high strength biocompatible material or a polymer such as PEEK, PEKK, and other polymeric materials know to be biocompatible and having sufficient strength. In some embodiments, the materials used to construct the bone fusion device include using additives, such as carbon fibers for better performance of the materials under various circumstances. The base biocompatible material is often textured or coated with a porous material conducive to the growth of new bone cells on the bone fusion device 100. The bone fusion device 100 is able to have several conduits or holes 120 (also see FIG. 2) which permit the bone graft material to be inserted into the device 100 and to contact the vertebral bone before or after the device 100 has been inserted between the vertebrae of the patient. The bone graft material and the surface texturing of the device 100 encourage the growth and fusion of bone from the neighboring vertebrae. The fusion and healing process will result in the bone fusion device 100 aiding in the bridging of the bone between the two adjacent vertebral bodies of the spine which eventually fuse together during the healing period.

As further illustrated in FIGS. 1A and 1B, plates 130 are located on opposing sides of the bone fusion device 100. The plates 130 are shaped so that their outer surface is substantially flush with the frame 114 of the bone fusion device 100 in a nonextended position. Internally, the plates 130 have a full or partial central rib 124 and an angled inner surface. Specifically, the central rib 124 is configured to provide further outer surface area and structural support to the plates 130. Further, each plate 130 is shaped such that one or more angled surfaces 123 of the plate 130 for extending the plate 130 have end thicknesses that are larger than their middle thicknesses such that the thickness of the angled surfaces 123 gradually increases while going from the middle to the ends of the plate 130. A positioning component 108 within the frame 114 of the bone fusion device 100 comprises a positioning aperture 134, a first screw 102 and a second screw 104 coupled together (see FIGS. 4A and 4B). The positioning aperture 134 is configured to receive a drive/engaging mechanism 808 of a tool 602 (see FIGS. 6A-6G and 8) such that the tool 602 is able to rotate or otherwise manipulate the positioning component 108. The positioning aperture 134 is able to comprise numerous shapes and sizes as are well known in the art. The first screw 102 is threaded opposite of the second screw 104. For example, if the first screw 102 is left threaded, the second screw 104 is right threaded or vice-versa. Furthermore, the first screw 102 (see FIG. 2) is of a slightly different size than the second screw 104. The positioning component 108 is coupled to a first extending block 110 and a second extending block 112, each having a pair of rib slots 126 configured to receive the central ribs 124 of the plates 130 (see FIG. 1B). Specifically, the rib slots 126 are sized such that they permit the central ribs 124 to slide into and out of the slots 126 (depending on the position of the blocks 110, 112) such that when positioned within the slots 126, the blocks 110, 112 are able to support the plates 130 against torsional forces by holding and supporting the central ribs 124.

Further, the first extending block 110 is coupled to the first screw 102 and the second extending block 112 is coupled to the second screw 104, and the first extending block 110 and the second extending block 112 are positioned in the middle of the bone fusion device 100 in the compact position. When the positioning component 108 is turned appropriately, the extending blocks 110 and 112 each travel outwardly on their respective screws 102 and 104. As the extending blocks 110 and 112 travel outwardly, they push the plates 130 outward and the central ribs 124 slide within the rib slots 126. In other words, the inner plate surface 123 when in contact with the extending blocks 110, 112 act in such a manner so as to push the respective plates 130 apart. Specifically, the angled surfaces 111 of each extending block 110, 112 are able to be in contact with the plate surfaces 123 and the center rib surface 121 is in contact with the extending block slot surface 125. Thus, the plates 130 will be fully extended when the extending blocks 110 and 112 reach the opposite ends of the screws 102, 104. To retract the plates 130, the positioning device 108 is turned in the opposite direction and the extending blocks 110 and 112 will each travel back to the middle on their respective screws 102 and 104 with the central ribs 124 within the rib slots 126 enabling the plates 130 to move into the retracted position due to gravity or another downward force. When the extending blocks 110 and 112 are positioned in the middle of the bone fusion device 100, the plates 130 are compact and are within the frame 114 of the bone fusion device 100. In some embodiments, the extending blocks 110 and 112 are coupled to the plates 130 such that they apply the needed downward force to retract the plates. Alternatively, the plates 130 are able to be biased with a biasing mechanism that applies the downward force needed to cause the plates 130 to retract when enabled by the position of the extending blocks 110, 112. For example, one or more springs are able to be coupled to the plates 130, wherein the springs apply a retraction biasing force to the plates 130 that causing the plates to retract when enabled by the extending blocks 110, 112.

It is contemplated that the operation of the device 100 is able to be reversed such that the plates 130, extending blocks 110, 112, and positioning components 108 are configured such that the extending blocks 110, 112 travel inwardly to extend the plates 130 into the extended position and travel outwardly to retract the plates 130 into the compact position. Further, it is contemplated that the positioning component 108 is able to be a non-rotational or other type of force generating mechanism that is able to move the extending blocks 110, 112. For example, the positioning component 108 is able to be a mechanism were a non-rotational movement (e.g. in/out of the device 100) causes the movement of the extending blocks 110, 112. In any case, the nonextended plates 130 of the bone fusion device 100 provide a compact assembly that is suitable for insertion into the patient's body through a open, or minimally invasive surgical procedure. As used herein, an open or a minimally invasive procedure comprises a procedure wherein a smaller surgical incision is employed as compared to the size of the incision required for conventional invasive surgery, for example, arthroscopic procedures. Moreover, minimally invasive procedures minimize or eliminate the need for excessive retraction of a patient's tissues such as muscles and nerves, thereby minimizing trauma and injury to the muscles and nerves and further reducing the patient's recovery time.

Figure 3:
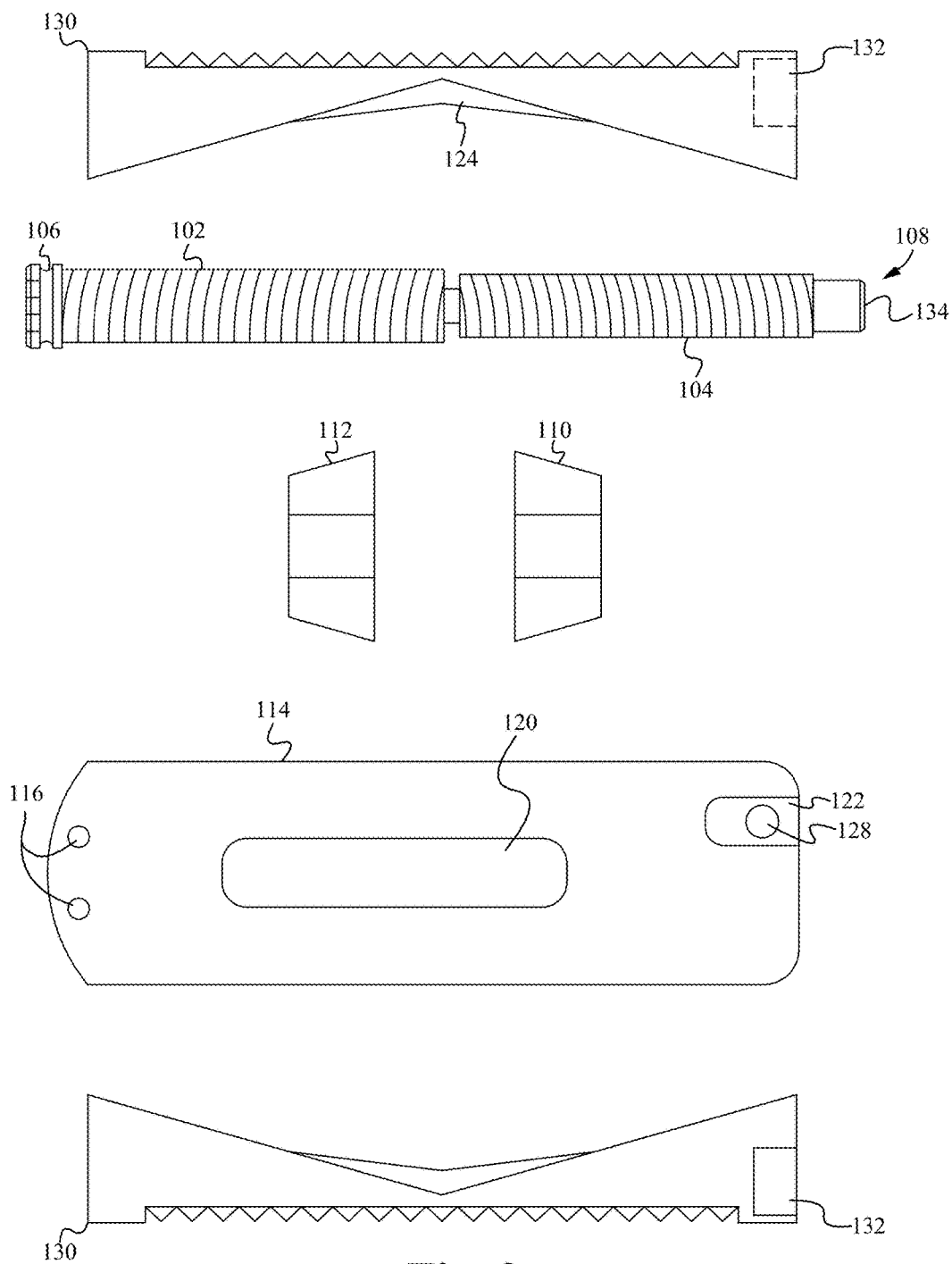
FIG. 3 illustrates a cross-sectional view of components of the bone fusion device according to some embodiments.

As the positioning component 108 is rotated causing the extending blocks 110 and 112 to move closer to the ends of the respective screws 102 and 104, the extending blocks 110 and 112 push the plates 130 outward causing the plates 130 to assert pressure against surrounding bones and securing the bone fusion device 100 in place. When the extending blocks 110 and 112 reach as close to the end of the positioning components 108 as allowed, the plates 130 are fully extended. Furthermore, since the extending blocks 110 and 112 travel along the positioning components 108, along the threads of the screws 102 and 104, very precise positions of the plates 130 are able to be achieved. The plates 130 are able to have serrated edges or teeth 136 to further increase the bone fusion device's gripping ability and therefore ability to be secured in place between the bones for both a long-term purchase and a short-term purchase. In some embodiments, the serrated edges or teeth 136 are able to be in a triangular or form a triangular wave formation as shown in FIG. 3. Alternatively, the serrated edges or teeth 136 are able to be filleted, chamfered, or comprise other teeth shapes or edge waves as are well known in the art.

To secure the bone fusion device 100 in place, a user generally utilizes an insertion instrument such as a screw driver to turn the positioning components 108. Screw drivers unfortunately have the ability to slip out of place. When performing surgery near someone's spine, it is preferable to prevent or at least minimize the slipping ability. Further, it is necessary to ensure that the surgeon is able to precisely place and control the device via a robust connection to the device. To do so, channels 122 having gripping apertures 128 are implemented to receive gripping fingers of a tool/insertion instrument (not shown) such that the tool cannot slip out of place during operation. Specifically, the channels 122 are sized to receive the fingers to prevent the tool from moving laterally with respect to the head of the positioning components 108 and the gripping apertures 128 are sized to receive the fingertips of the fingers of the tool such that the fingers (and tool) are unable to unintentionally be pulled out of the channels 122 (and positioning components 108). In some embodiments, the channels 122 are offset such that when facing the positioning aperture 134, one channel 122 is proximate the top left of the device 100 and the other channel 122 is proximate the bottom right of the device 100. Alternatively, the channels 122 are able to positioned on other portions of the frame 114. In operation, a surgeon causes the fingers of the tool to spread as the are inserted into the channels 122, and then the surgeon causes the fingers to clamp together inserting the fingertips of the fingers into the gripping apertures 128 and fully securing the tool onto the device 100. Thus, the tool is unable to slip out of place and is only able to be removed upon the spreading of the fingers such that the fingertips are removed from the apertures 128 and the fingers are removed from the channels 122. Furthermore, if the device 100 is next to relatively immovable tissue (e.g. bone, ligament or tendon under load), then this device 100 will still be able to disengage, whereas one that relies on clamping by bending two rods together will not work if one of the rods is restricted by the relatively immovable tissue.

Figure 2:
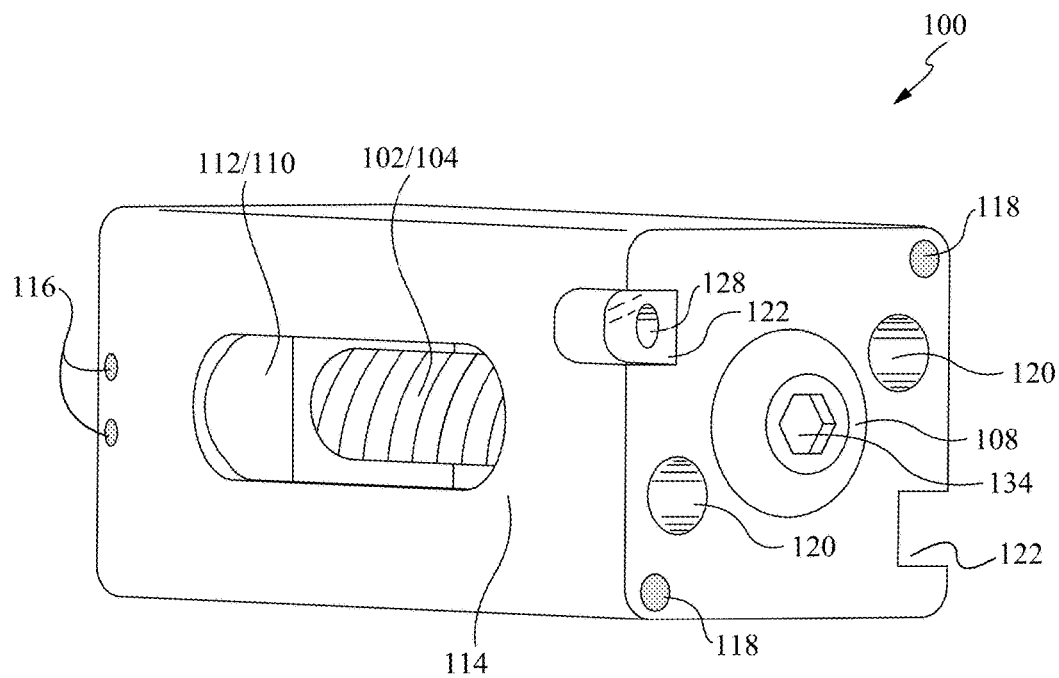
FIG. 2 illustrates a side perspective view of the bone fusion device according to some embodiments.
Figure 6A:
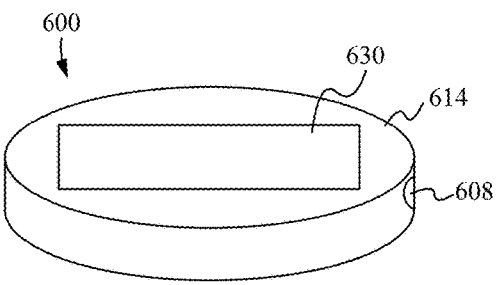
FIG. 6A illustrates a top view of a bone fusion device according to some embodiments.
Figure 6B:
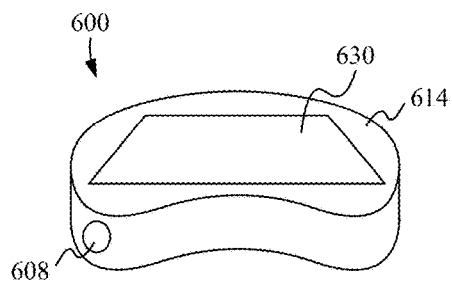
FIG. 6B illustrates a top view of a bone fusion device according to some embodiments.
Figure 6C:
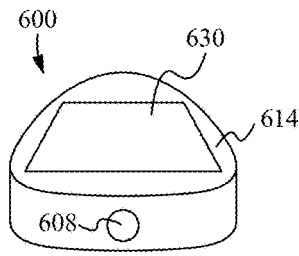
FIG. 6C illustrates a top view of a bone fusion device according to some embodiments.

FIG. 2 illustrates a side perspective view of the bone fusion device 100 according to some embodiments. The bone fusion device 100 utilizes the positioning components 108 comprising the first screw 102 and the second screw 104 to move the first extending block 110 and the second extending block 112 outwardly from the middle of the bone fusion device 100 towards its ends. The positioning component 108 is held in place but permitted to turn utilizing one or more first pins 116. The one or more first pins 116 are secured within a retaining groove 106 (FIG. 3) of the positioning component 108. The extending blocks 110 and 112 force the plates 130 to either extend or retract depending on where the extending blocks 110 and 112 are positioned. As described above, the plates 130 are able to have serrated edges or teeth 136 to further increase gripping ability. The plates 130 are each coupled to the frame 114 of the bone fusion device 100 by one or more pin slots 132 (FIGS. 3 and 4A) and one or more second pins 118 wherein the one or more second pins 118 fit within the one or more pin slots 132 and are able to travel along the interior of the one or more pin slots 132. In some embodiments, each plate 130 is secured with a single second pin 118 and pin slot 132. Alternatively, one or more of the plates 130 are able to have multiple second pins 118 and pin slots 132. In some embodiments, the multiple pin slots 132 are able to be positioned at the corners of the plates 130 similar to the single pin slot 132 shown in FIG. 3. In some embodiments, the multiple pin slots 132 of plates 130 are symmetric such that any plate 130 is able to be placed on the top or bottom of the bone fusion device 100. Alternatively, the pin slots 132 of the plates 130 are able to be positioned anywhere on the plate 130 and/or be positioned asymmetrically. The holes/conduits 120 within the plates 130 allow the bone graft material to contact the vertebral bone after the device 100 has been inserted between the vertebrae of the patient. A set of holes/conduits 120 within the frame 114 also allow bone graft material to be inserted within the bone fusion device 100 after the bone fusion device 100 has been placed. The channels 122 having gripping apertures 128 implemented to receive a tool are shown as well. Alternatively, the gripping apertures 128 are able to be omitted.

FIG. 3 illustrates a cross-sectional view of components of the bone fusion device 100 according to some embodiments. As described above, the positioning component 108 comprises a first screw 102 and a second screw 104 wherein the first screw 102 is threaded differently than that of the second screw 104. Furthermore, the first screw 102 is of a slightly different size than the second screw 104. For example, in some embodiments the first screw 102 is an 8-32 screw and the second screw is a 6-32 screw. A retaining groove 106 is utilized to secure the positioning component 108 in place. In some embodiments, the retaining groove 106 is positioned opposite the end of the positioning component 108 having the positioning aperture 134. To ensure that the tool does not slip while turning the positioning component 108, the channels 122 having fingertip gripping apertures 128 are utilized to secure the tool as described above. Alternatively, the fingertip gripping apertures 128 are able to be omitted and the channels 122 are able to secure the tool as described above. A first extending block 110 and a second extending block 112 are utilized with the positioning component 108 to extend and compact one or more of plates 130. The first extending block 110 has an internal opening and threading to fit around the first screw 102. The second extending block 112 has an internal opening and threading to fit around the second screw 104. The frame 114 of the bone fusion device 100 contains a set of holes/conduits 120 within the frame 114 for allowing bone graft material to be inserted. Furthermore, one or more first pins 116 secure the positioning component within the frame 114. One or more second pins 116 in conjunction with one or more pin slots 132 secure the plates 130 to the frame 114.

Figure 4A:
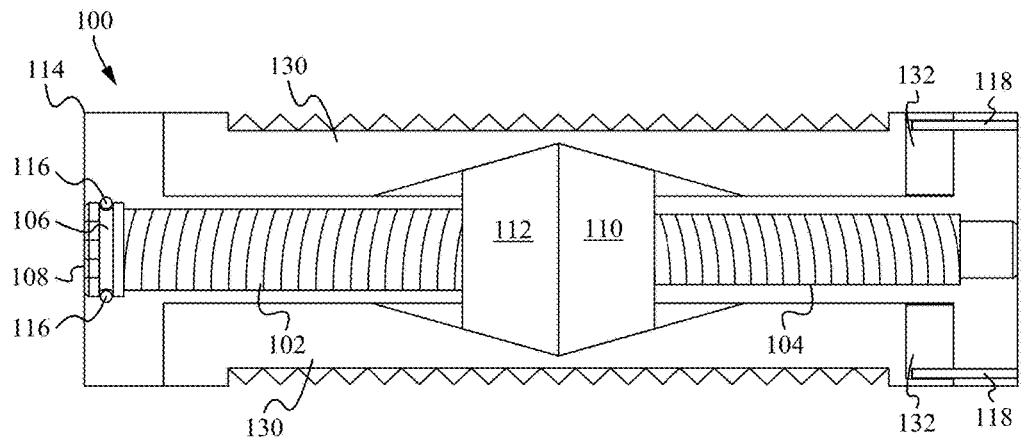
FIG. 4A illustrates a cross sectional view of the bone fusion device with the plates compacted according to some embodiments.

FIG. 4A illustrates a cross sectional view of the bone fusion device 100 with the plates retracted according to some embodiments. When the extending blocks 110 and 112 are positioned in the middle of the positioning component 108 with the first screw 102 and the second screw 104, the plates 130 are positioned within the frame 114 of the bone fusion device 100 with the central ribs 124 slid within the rib slots 126. The retaining groove 106 holds the positioning component 108 in place with one or more first pins 116. The plates 130 are coupled to the frame 114 of the bone fusion device 100 using the one or more slots 132 and the one or more second pins 118 wherein the one or more second pins 118 fit within the one or more slots 132 and are able to travel/slide along the interior of the one or more slots 132.

Figure 4B:
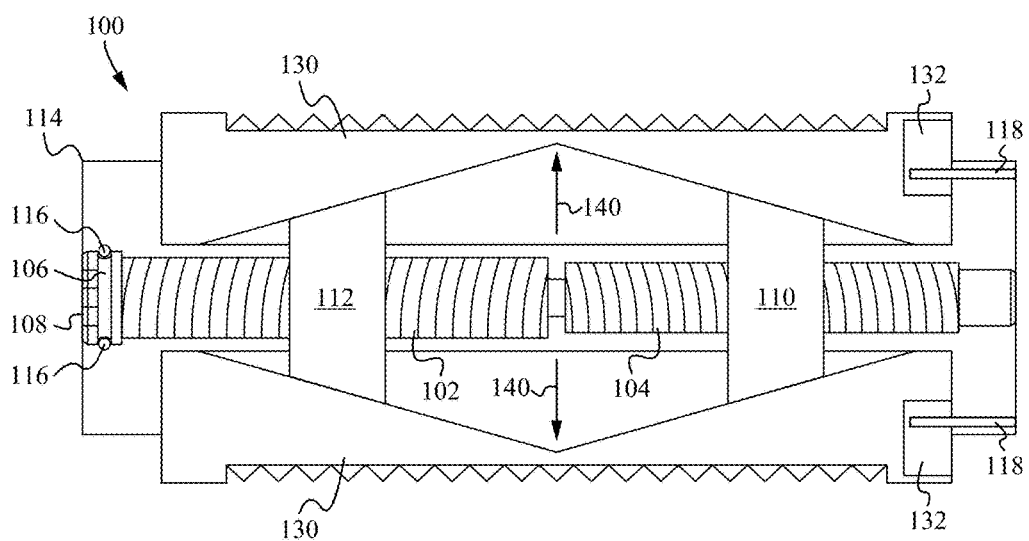
FIG. 4B illustrates a cross sectional view of the bone fusion device with the plates extended according to some embodiments.

FIG. 4B illustrates a cross sectional view of the bone fusion device 100 with the plates extended according to some embodiments. As shown in FIG. 4A, the bone fusion device 100 is compressed/contracted when the extending blocks 110 and 112 are in the middle of the bone fusion device 100. As a user turns the positioning component 108 via the positioning aperture 134, the extending blocks 110 and 112 gradually move outward from the middle. If the user turns the positioning component 108 in the opposite direction, the extending blocks move back towards the middle. As the extending blocks 110 and 112 are moving outward, the central ribs 124 slide out of the rib slots 126 and the extending blocks 110, 112 push on the plates 130. Alternatively, the cental ribs 124 and/or rib slots 126 are able to be configured such that the central ribs 124 are fully within the rib slots 126, fully removed from the rib slots 126, or somewhere in between at any point along the path of the extending blocks 110, 112 from the center of the device to the ends of the device. The plates 130 extend because the extending blocks 110 and 112 exert force against the angled plates 130 outwardly as shown by the arrows 140. When the extending blocks 110 and 112 are positioned near the ends of the bone fusion device 100, the plates 130 extend beyond the frame 114 of the bone fusion device 100 and ultimately secure the bone fusion device 100 between two bones. With the plates 130 coupled to the frame 114 of the bone fusion device 100 by the one or more slots 132 and the one or more second pins 118, the plates 130 are able to extend beyond the frame 114 of the bone fusion device 100 as the one or more second pins 118 travel within the interior of the one or more slots 132.

In operation, the bone fusion device 100 is initially configured in a compact position such that the extending blocks 110, 112 are located in the middle of the bone fusion device 100 thereby allowing the plates 130 to rest within the frame 114 of the bone fusion device 100. The compact bone fusion device 100 is then inserted into position within the patient. The surgeon is able to then the expand the bone fusion device 100 by rotating the positioning component 108 which moves the extending blocks 110, 112 towards the opposing ends of the bone fusion device 100—one near the head of the positioning component 108 and the other towards the tail of the positioning component. As the extending blocks 110, 112 move away from the middle, the plates 130 are pushed outwardly from the pressure of the extending blocks 110, 112 against the angled plates 130. Initially, the central ribs 124 of the plates 130 remain at least partially within the rib slots 126 of the extending blocks 110, 112 such that the blocks 110, 112 are able to resist torsional forces on the plates 130 and/or device 100. Gradually, the central ribs 124 slide out of the rib slots 126 as the extending blocks 110, 112 approach the ends of the positioning component 108. Alternatively, the central ribs 124 are able to be configured such that they remain at least partially within the rib slots 126 as the extending blocks 110, 112 approach the ends of the positioning component 108. Eventually the extending blocks 110, 112 exert a satisfactory force between the extended plates 130 and the bones to be fused. At that point the bone fusion device 100 is able to remain in place. Thereafter, material for fusing the bones together is inserted through the holes and openings 120 within the bone fusion device 100. Alternatively, the insertion of the material for fusing the bones together is able to be omitted.

Figure 5:
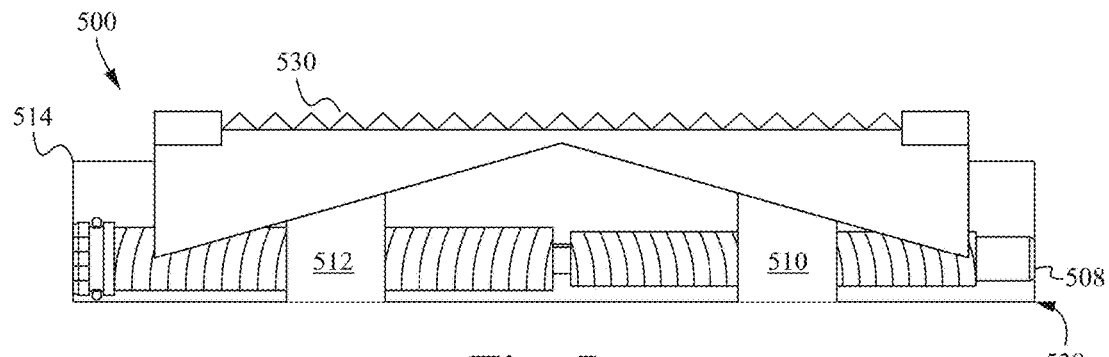
FIG. 5 illustrates a profile view of a bone fusion device having a single plate extension/retraction mechanism according to some embodiments.

FIG. 5 illustrates a bone fusion device 500 having a single plate extension/retraction mechanism according to some embodiments. The bone fusion device 500 shown in FIG. 5 is substantially similar to the bone fusion device 100 except for the differences described herein. In particular, the bone fusion device 500 comprises a half frame 514, one or more half extending blocks 510, 512, a plate 530 and positioning component 508. Similar to the bone fusion device 100, the half extending blocks 510, 512 are coupled around the positioning component 508 such that when the positioning components 508 are turned, the blocks 510, 512 move outwards causing the plate 530 to move to the extended position. The half frame 514 comprises a plate aperture (see FIG. 1A) for receiving the plate 530 and a solid floor 538 opposite the plate aperture. In some embodiments, the floor 538 is able to have one or more floor holes/conduits for receiving/distributing grafting material into and out of the device 500. In some embodiments, the device 500 is sized such that when the plate 530 is in the compact/retracted position the distance between the top of the plate 530 and the floor 538 is less than or equal to 5 mm, and when the plate 530 is in the extended position the distance between the top of the plate 530 and the floor 538 is less than or equal to 7 mm. Alternatively, the device 500 is sized such that when the plate 530 is in the compact/retracted position the distance between the top of the plate 530 and the floor 538 is in the range of 5 mm to 13 mm and when the plate 530 is in the extended position the distance between the top of the plate 530 and the floor 538 is in the range of 7 mm to 22 mm. Alternatively, other sizes of the device 500 are contemplated as are well known in the art. Thus, by including only a single plate 530, the height of the device 500 is able to be minimized. As a result, the bone fusion device 500 enables surgeons to use smaller incisions as well as to fit the bone fusion device 500 into smaller places and increasing the versatility of the device 500. Additionally, it should be noted that the single plate extension/retraction mechanism described in FIG. 5 is able to replace each of the dual or multiple plate extension/retraction mechanisms described herein wherein the devices having dual plate extension/retraction mechanisms are essentially halved (except for the positioning component) such that only one plate is remaining.

Figure 6D:
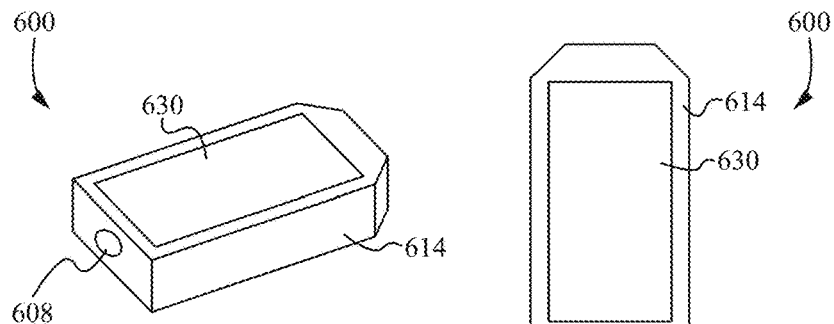
FIG. 6D illustrates a top and perspective view of a bone fusion device according to some embodiments.
Figure 6E:
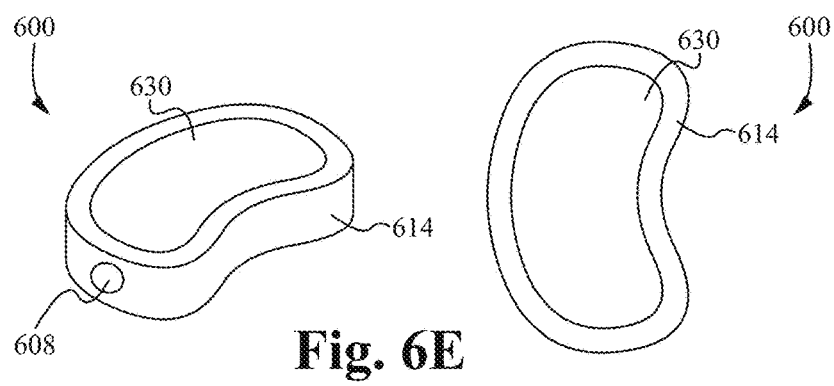
FIG. 6E illustrates a top and perspective view of a bone fusion device according to some embodiments.
Figure 6F:
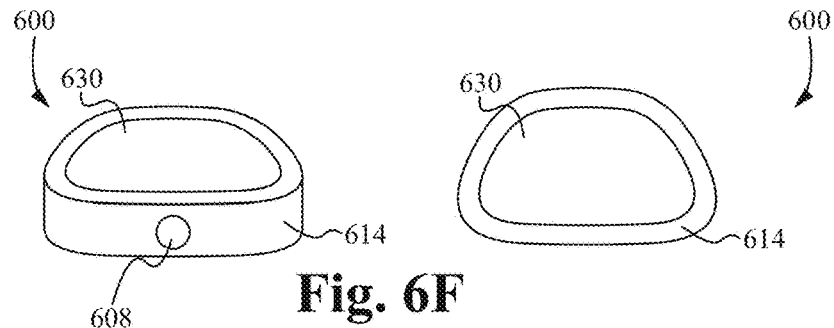
FIG. 6F illustrates a top and perspective view of a bone fusion device according to some embodiments.
Figure 6G:
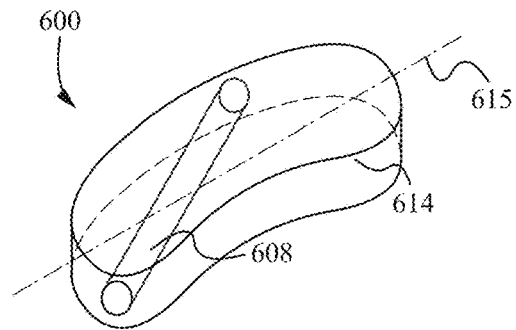
FIG. 6G illustrates a perspective view of a bone fusion device according to some embodiments.

FIGS. 6A-6G illustrate top and perspective views of a bone fusion device 600 according to some embodiments. Although one or more of the components discussed above are omitted, the bone fusion devices 600 shown in FIGS. 6A-6G are substantially similar to the bone fusion device 100 except for the differences described herein. As shown in FIGS. 6A-6G, the bone fusion device 600 comprises a positioning component/element 608 one or more plates 630 and a frame 614. Specifically, the frame 614 comprises an oval shaped (FIG. 6A), kidney shaped (FIG. 6B), round shaped (FIG. 6C), rectangular shaped (FIG. 6D), banana shaped (FIG. 6E) or otherwise shaped (FIG. 6F) top/bottom view profile such that the shape of the top/bottom view profile of the frame 614 is substantially similar to the shape of the horizontal cross-section or top/bottom view profile of one or more vertebrae. Alternatively, the top/bottom view profile of the frame 614 is able to comprise one or more other shapes that substantially match top/bottom view profiles of bones that are to be fused to the bone fusion device 600. Alternatively, the top profile of the plates 630 are able to be shaped as described herein, wherein the frame 614 remains the standard shape as described above. In some embodiments, the top view profile of the plates 630 are shaped substantially similar to the top/bottom profile of the frame 614. For example, as shown in FIGS. 6D-6F, the plates 630 have rounded edges to match the perimeter of the frames 614. Alternatively, the top profile of the plates 630 is able to comprise other shapes as are well known in the art. In some embodiments, the top view profile shapes of the frame 614 are between 15 and 25 mm along the anterior/posterior axis and between 20 and 45 mm along the lateral axis. Alternatively, other dimensions are envisioned. For example, for bone fusion devices designed for cervical spinal bones, the frame 614 is able to be less than 15 mm along the anterior/posterior axis and less then 20 mm along the lateral axis. Alternatively, the frame 614 is able to be 55 mm or longer along the lateral axis (typically for extreme lateral lumbar interbody fusion). In some embodiments, as shown in FIG. 6G, the positioning components 608 are able to be non-parallel with the elongated lateral dimension/axis 615 of the frame 614 and/or tabs 630. As a result, the bone fusion device 600 provides the advantage of substantially matching the horizontal profiles of the bones to be fused, thereby increasing the strength and efficiency of the fusion process. Further, the profile shapes provide the advantage of enabling a user to select a bone fusion device 600 with a top profile shape whose orientation matches the insertion orientation of the operation. Further, the angles at which the positioning components 608 are oriented with respect to the elongated axis 615 of the frame 614 is able to be selected to match the angle of access provided by a desired operation. As a result, the bone fusion device 600 does not need to be turned to be in the proper orientation between the bones of the patient whether the procedure is anterior, posterior, lateral, far-lateral or transforaminal lumbar interbody fusion.

Figure 7:
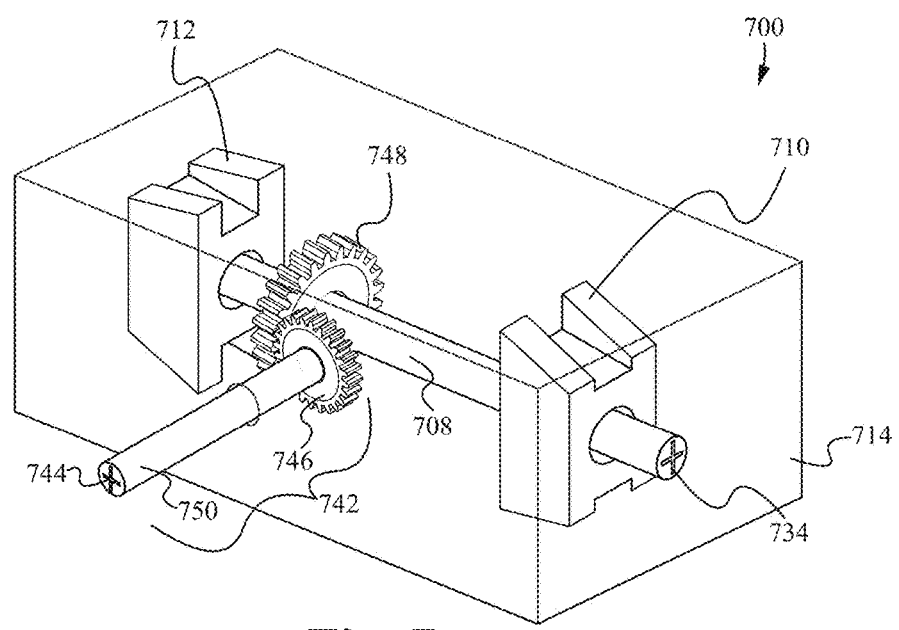
FIG. 7 illustrates a cross sectional perspective view of a bone fusion device having an angled positioning components according to some embodiments.

FIG. 7 illustrates a cross sectional perspective view of a bone fusion device 700 having an angled positioning components according to some embodiments. The bone fusion device 700 shown in FIG. 7 is substantially similar to the bone fusion device 100 except for the differences described herein. Specifically, as shown in FIG. 7, the bone fusion device 700 comprises a frame 714 housing one or more extending blocks 710, 712, positioning components 708 and angled positioning components 742. The angled positioning components 742 comprise a positioning shaft 750, one or more screw gears 748, one or more shaft gears 746 and an angled positioning aperture 744. The screw gear 748 is coupled to the positioning components 708 such that when the screw gear 748 is rotated, the positioning components 708 are also rotated. One end of the positioning shaft 750 is coupled to the shaft gear 746 and the other end of the positioning shaft 750 is coupled to the angled positioning aperture 744 such that a drive mechanism (not shown) is able to rotate the shaft gear 746 (via the positioning shaft 750) by rotating the angled positioning aperture 744. Further, the shaft gear 746 and the screw gear 748 are in communication with each other such that when a drive mechanism rotates the shaft gear it is also able to rotate the positioning components 708. Alternatively, the angled positioning components 742 are able to comprise other types of frictional torsion transfer systems as are well known in the art.

Thus, a user is able to control the extension and retraction of the plates (not shown) by rotating the angled positioning components 742. In some embodiments, the angled positioning components 742 is positioned such that the shaft 750 is substantially perpendicular to the positioning components 708. Alternatively, the angled positioning components 742 is able to be positioned such that the shaft 750 forms any angle between 0 and 90 degrees with the positioning components 708. In some embodiments, the angled positioning aperture 744 is able to replace the positioning aperture 134 such that the positioning element 708 is only able to be rotated using the angled positioning aperture 744. Alternatively, the bone fusion device 700 comprises both a positioning aperture 734 and the angled positioning aperture 744 such that either aperture 734, 744 is able to be used to position the one or more plates 730. In some embodiments, the shaft gears 746 and/or screw gears 748 comprise disk gears that interlock via interlocking teeth. Alternatively, the shaft gears 746 and/or screw gears 748 are able to comprise one or more of disk gears, beveled gears, worm gears and/or other types of gears as are well known in the art. Thus, the bone fusion device 700 provides the advantage of allowing the plates 730 to be extended from angles other than parallel to the positioning components 708, which is critical in procedures where the device 700 is to be inserted from varying angles such as, for example, anterior lumbar interbody fusion, lateral lumbar interbody fusion or transforaminal lumbar interbody fusion. Additionally, it should be noted that the differences to the bone fusion device 700 described in FIG. 7 are able to be incorporated with and/or replace components of each of the other bone fusion devices described herein.

Figure 8:
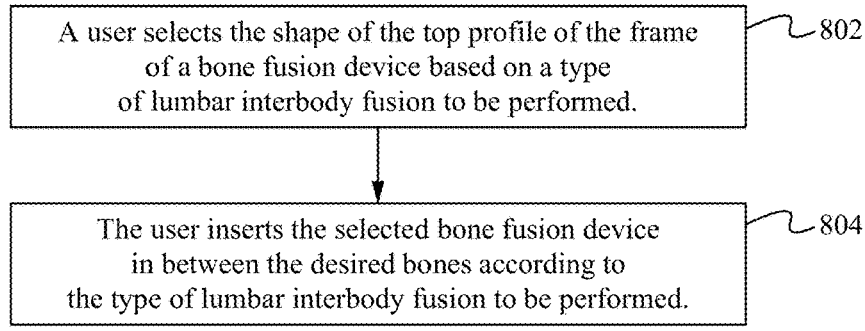
FIG. 8 illustrates a flowchart directed to a method of using a bone fusion device according to some embodiments.

A method of using the bone fusion device 600 according to some embodiments is illustrated by the flow chart in FIG. 8. A user selects the shape of the top profile of the frame 614 of a bone fusion device 600 based on a type of lumbar interbody fusion to be performed at the step 802. In some embodiments, the user selects an elongated oval shape frame 614 based on the type being extreme lateral lumbar interbody fusion. Alternatively, the user selects a kidney or rounded shape frame 614 based on the type being anterior lumber interbody fusion. In some embodiments, the user selects the shape of the top profile of the frame 614 of a bone fusion device 600 based on a horizontal profile of the bone or bones to be fused to the device. For example, a bone fusion device is able to be selected because the device 600 has a top profile shape that substantially matches the shape of the horizontal profile of a cervical spinal bone or bones to be fused with. The user inserts the selected bone fusion device 600 in between the desired bones according to the type of lumbar interbody fusion to be performed at the step 804. In some embodiments, the bone fusion device 600 is able to be positioned offset from the center of the adjacent bones and/or discs. Thus, the method of using the bone fusion device 600 provides the advantage of enabling a user to select a top profile of the frame 614 of the bone fusion device 600 based on the type of procedure thereby increasing the effectiveness of the procedure. Additionally, it should be noted that one or more of the steps of the above method are able to be omitted or combined with the other methods described herein.

Figure 9:
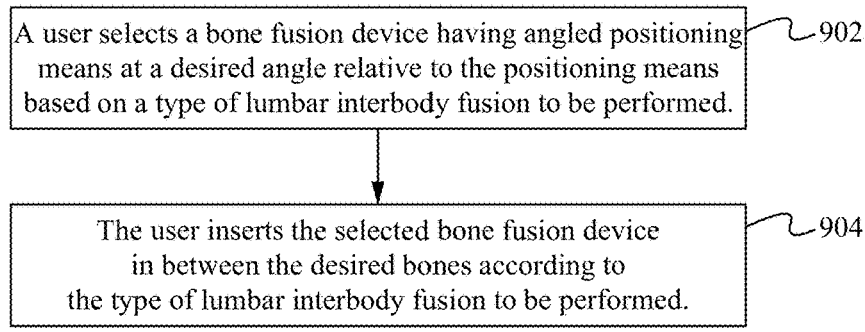
FIG. 9 illustrates a flowchart directed to a method of using a bone fusion device according to some embodiments.

A method of using the bone fusion device 700 according to some embodiments is illustrated by the flow chart in FIG. 9. A user selects a bone fusion device 700 having angled positioning components 742 at a desired angle relative to the positioning components 708 based on a type of lumbar interbody fusion to be performed at the step 902. In some embodiments, the user selects angled positioning components 742 that are substantially parallel to the positioning components 708 based on the type being anterior lumbar interbody fusion. In some embodiments, the user selects a bone fusion device 700 having angled positioning components 742 at a desired angle relative to the positioning components 708 based on the shape of the top profile of the frame 614 of a bone fusion device 600 and the type of lumbar interbody fusion to be performed. The user inserts the selected bone fusion device 700 in between the desired bones according to the type of lumbar interbody fusion to be performed at the step 904. Thus, the method of using the bone fusion device 700 provides the advantage of enabling a user to select a bone fusion device 700 having angled positioning components 742 that form a desired angle with the positioning components 708 of the bone fusion device 700 based on the type of procedure thereby increasing the effectiveness of the procedure. Additionally, it should be noted that one or more of the steps of the above method are able to be omitted or combined with the other methods described herein.

Figure 10A:
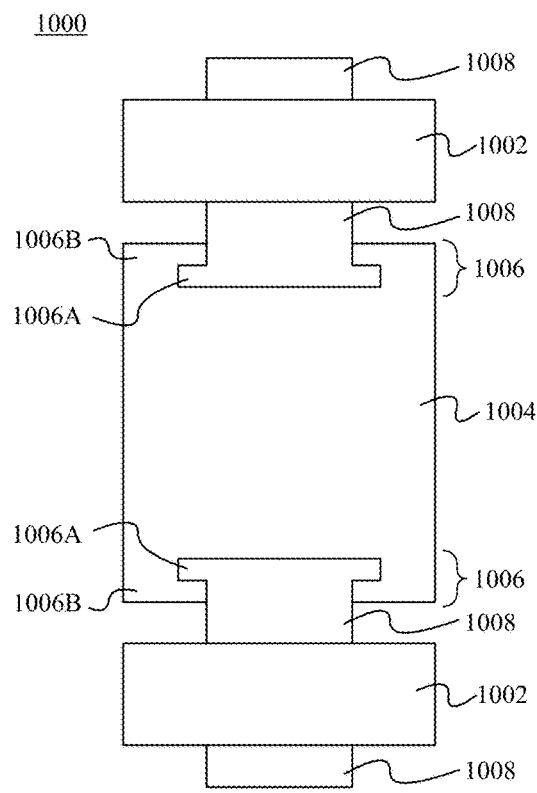
FIG. 10A illustrates a lateral view of a bone fusion system according to some embodiments.

FIG. 10A illustrates a lateral view of a bone fusion system 1000 according to some embodiments. As shown in FIG. 10A, the bone fusion apparatus 1000 comprises one or more bone fusion device bodies 1002 having one or more plates 1008 and one or more device fasteners 1006A, and a replacement body 1004 having one or more body fasteners 1006B. Alternatively, the bone fusion devices 1002 are able to comprise the body fasteners 1006B and the replacement body 1004 is able to comprise the device fasteners 1006A. The one or more device fasteners 1006A are coupled to the top of one or more of the plates 1008 and the one or more body fasteners 1006B are coupled to the top and/or bottom of the replacement body 1004. As a result, a user is able to detachably couple one or more of the devices 1002 to the replacement body 1004 by detachably coupling the device fasteners 1006A to the body fasteners 1006B. In some embodiments, a plurality of replacement bodies 1004 are directly coupled together, wherein bone fusion devices 1002 are coupled to one or both of the unoccupied ends of the directly coupled replacement bodies 1004. In some embodiments, the replacement bodies 1004 are able to have varying heights such that the bodies 1004 are able to singly or in combination replace one or more bones of a variety of heights. For example, the replacement bodies 1004 are able to be used for replacing bones when performing a corpectomy due to cancer or infection. In some embodiments, the fasteners 1006A, 1006B comprise a rail/slot fastening mechanism. Alternatively, the fasteners 1006A, 1006B are able to comprise other types of permanent or detachable fasteners as are well known in the art. In some embodiments, the replacement body 1004 is hollow. In some embodiments, the bone fusion device bodies 1002 comprise one or more fasteners 1006A, 1006B in addition to or instead of the fasteners 1006A, 1006B on the plates 1008. In some embodiments, the replacement body 1004 has a top profile that is substantially similar to the horizontal profile of the bone that is to be replaced. Alternatively, the replacement body 1004 is able to be solid and/or have other top profile shapes as are well known in the art. The one or more bone fusion devices 1002 are able to be substantially similar to the bone fusion device 100 except for the differences described herein.

Figure 10B:
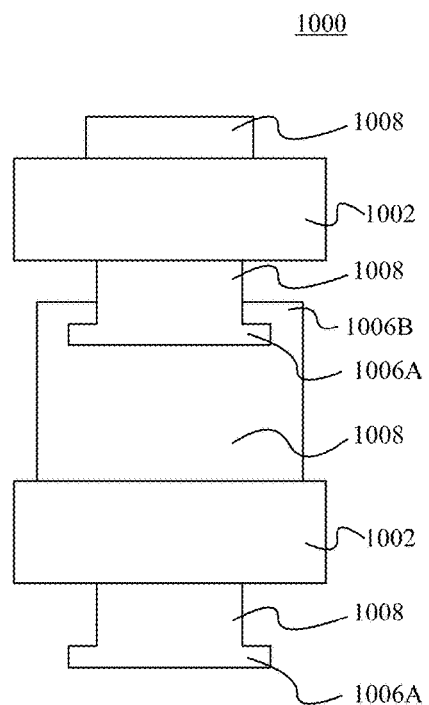
FIG. 10B illustrates a lateral view of a bone fusion system according to some embodiments.
Figure 10C:
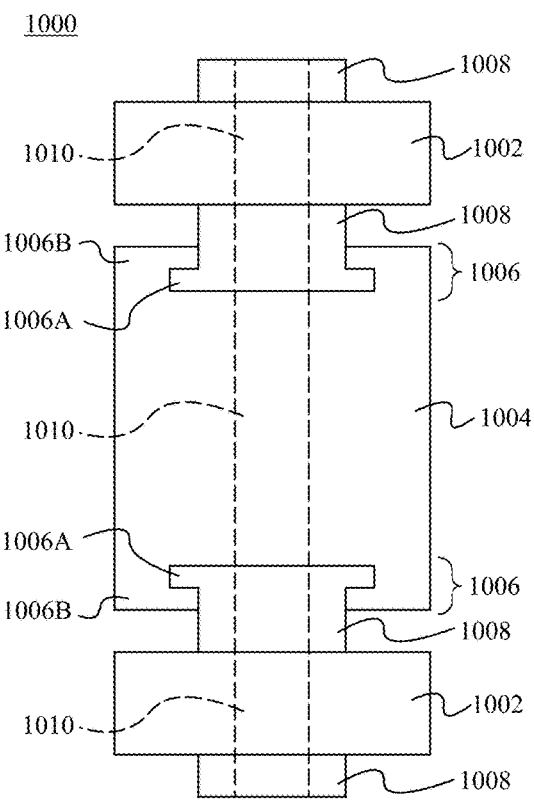
FIG. 10C illustrates a lateral view of a bone fusion system having one or more channels according to some embodiments.

Alternatively, as shown in FIG. 10B, the replacement body 1004 is able to be omitted such that the system 1000 comprises a plurality of bone fusion devices 1002 coupled together directly. Specifically, as shown in FIG. 10B each of the plates 1008 of each of the bone fusion devices 1002 are able to comprise either a device fastener 1006A or a body fastener 1006B such that plates 1008 with a body fastener 1006B are able to directly couple to plates 1008 with a device fastener 1006A. In some embodiments, only one of the plates 1008 of a device 1002 comprises a fastener 1006A, 1006B. In some embodiments, one or more of the devices 1002 comprise at least one plate 1008 having a device fastener 1006A and at least one plate 1008 having a body fastener 1006B. In some embodiments, one or more of the devices 1006 comprise a pair of plates 1008 both having either a device fastener 1006A or a body fastener 1006B. In some embodiments as shown in FIG. 10C, the fusion devices 1002 and/or the replacement bodies 1004 are able to comprise one or more channels 1010 such that when the fusion devices 1002 and/or replacement bodies 1004 are coupled together one or more of the channels 1010 are able to align or be in communication and thereby form one or more elongated channels that traverses across all or part of the system 1000. In particular, the alignment and/or communication of the channels 1010 enables bone grafting or other types of material to be inserted in to the elongated channels in order to better promote bone growth and the healing process.

Figure 11:
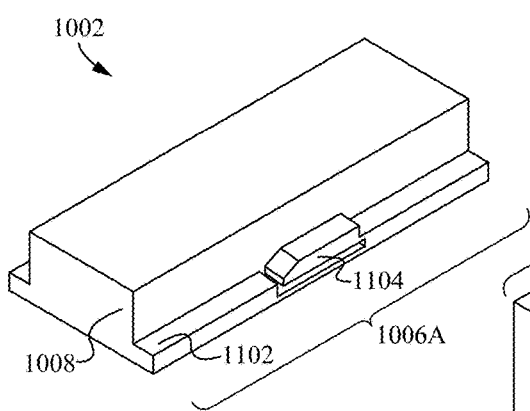
FIG. 11 illustrates a detailed perspective view of a device fastener according to some embodiments.
Figure 12:
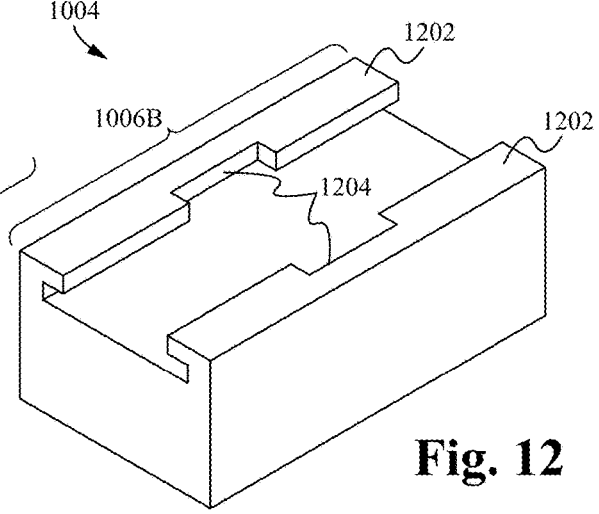
FIG. 12 illustrates a detailed perspective view of a body fastener according to some embodiments.

FIGS. 11 and 12 illustrate detailed perspective views of the device fastener 1006A and the body fastener 1006B, respectively, according to some embodiments. Specifically, as shown in FIG. 11, the device fastener 1006A comprises one or more slats or slots 1102 and one or more snap-fit members 1104 on the one or more slots 1102. As shown in FIG. 12, the device fastener 1006B comprises one or more rails 1202 and one or more cutouts 1204 within the one or more rails 1202. The slots 1102 are sized such that they are able to slide under the rails 1202, wherein the snap-fit members 1104 are depressed into the slot 1102 until the snap-fit members 1104 reach the cutouts 1204 and "snap" into place within the cutouts 1204. As a result, the device fastener 1106A is securely detachably coupled to the body fastener 1006B wherein the interlocking of the rails 1202 and the slots 1102 prevent the fasteners from being pulled away from each other, and the snap-fit member 1104 and the cutouts 1204 prevent the slots 1102 from sliding out from under the rails 1202. Alternatively, the rails 1202 are able to comprise the snap-fit members 1104 and the slots are able to comprise the cutouts 1204. Alternatively, other locking mechanisms as are well known in the art are able to be used in combination with or in place of the snap-fit member 1104 and/or the cutouts 1204. Thus, the bone fusion system 1000 provides the advantage of enabling multiple devices 1002 to be coupled together via a replacement body 1004 in order to replace a degenerated bone and the adjacent discs. Additionally, it should be noted that the differences to the bone fusion devices 1002 described in FIGS. 10-12 are able to be incorporated with and/or replace components of each of the other bone fusion devices described herein.

Figure 13:
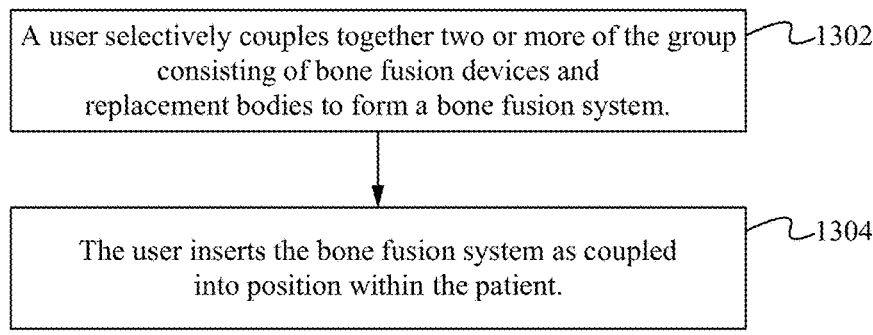
FIG. 13 illustrates a flowchart directed to a method of using the bone fusion system according to some embodiments.

A method of using the bone fusion system 1000 according to some embodiments is illustrated by the flow chart in FIG. 13. A user selectively couples together two or more of the group consisting of bone fusion devices 1002 and replacement bodies 1004 to form a bone fusion system 1000 at the step 1302. In some embodiments, the number of replacement bodies 1004 selected to be coupled together by the user is based on the height of the one or more bones and/or discs to be replaced. The user inserts the bone fusion system 1000 as coupled into position within the patient at the step 1304. Alternatively, the coupling of the bone fusion system 1000 is able to occur after one or more components of the system 1000 have been inserted into and/or positioned between the bones of the patient. Thus, the bone fusion system 1000 is able to provide the benefit of allowing surgeons to replaced one or more degenerated bones of varying heights by adjusting the height of the system 1000 and/or the component composition of the system 1000. Additionally, it should be noted that one or more of the steps of the above method are able to be omitted or combined with the other methods described herein.

Figure 14A:
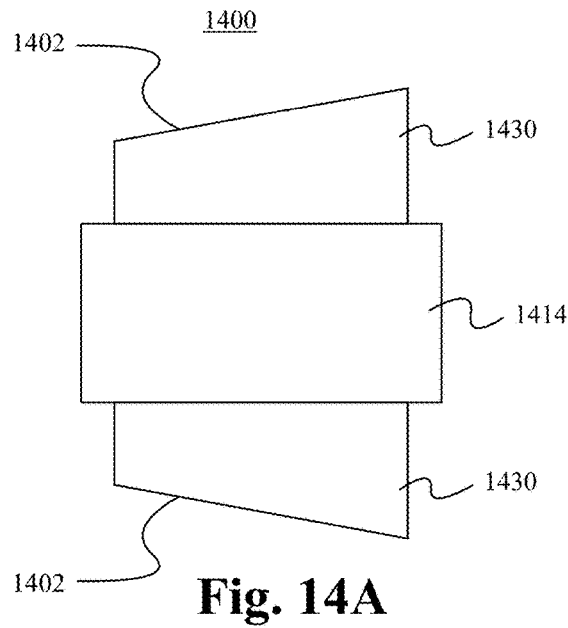
FIG. 14A illustrates a frontal view of a bone fusion device according to some embodiments.
Figure 14B:
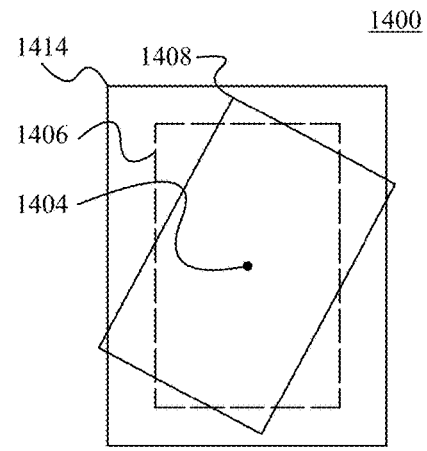
FIG. 14B illustrates a top view of a bone fusion device according to some embodiments.
Figure 14C:
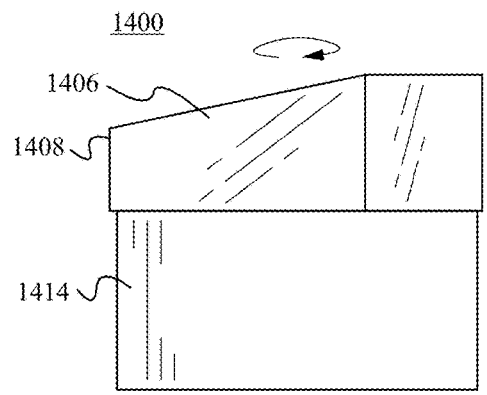
FIG. 14C illustrates a perspective top view of a bone fusion device according to some embodiments.

FIG. 14A illustrates a frontal view of a bone fusion device 1400 according to some embodiments. The bone fusion device 1400 shown in FIG. 14A is substantially similar to the bone fusion device 100 except for the differences described herein. Specifically, as shown in FIG. 14A, the bone fusion device 1400 comprises a frame 1414 and one or more plates 1430 having an angled or non-parallel top surface or top plane 1402 with respect to the top plane of the frame 1414 and/or the bottom plane of the plate 1430. In some embodiments, the angles of the top surface 1402 are along a single axis of the device 1400. For example, as shown in FIG. 14A the angles of the top surface 1402 are lateral with respect to a frontal view, making the angles well suited for correcting deformities such as scoliosis or other trauma repair. As another example, the angles of the top surface 1402 are able to be lateral with respect to a side view, making the angles well suited for lordosis/kyphosis adjustments. Alternatively, the angles of the top surface 1402 are able to be along multiple axes. In some embodiments, the angles and/or the orientation of the angles of each of the plates 1430 are substantially the same. Alternatively, one or more of the plates 1430 are able to have different angles and/or the orientation of the angles. In some embodiments, the plates 1430 are modular or interchangeable such that a user is able to select the plates 1430 to be included within the device 1400 based on the desired angle and/or orientation of the angle of the top surface 1402 of the plates 1430. In some embodiments, one or more of the plates 1430 with angled top surfaces 1402 are rotatable such that the orientation of the angled top surface 1402 is able to be adjusted once the plate has been extended. For example, as shown in FIGS. 14B and 14C, the plates 1430 are able to be rotated about an axis 1404 from an initial position 1406 parallel to the frame 1414 to a rotated position 1408 that is not parallel to the frame 1414. Thus, the orientation of the angled plates 1430 is able to be adjusted as needed to replace the degenerated discs and/or bones. In some embodiments, the axis 1404 is positioned at the center of the plates 1430. Alternatively, the axis 1404 is able to be off-center. In some embodiments, one or more of the plates 1430 are able to have a plurality of axis around which the plates 1430 are able to rotate. In some embodiments, one or more of the plates 1430 share one or more axes of rotation. Alternatively, one or more of the plates 1430 are able to have different axis of rotation than one or more of the other plates 1430. In some embodiments, the plates 1430 are unable to rotate and the orientation of the angled top surface 1402 is able to be adjusted by rotating the entire device 1400. Thus, the bone fusion device 1400 provides the advantage of enabling the angle and orientation of the plates to be adjusted to correct scoliosis an other spine/bone angle irregularities. Additionally, it should be noted that the components of the bone fusion device 1400 described in FIGS. 14A-14C are able to be incorporated with and/or replace components of each of the other bone fusion devices described herein.

Figure 15:
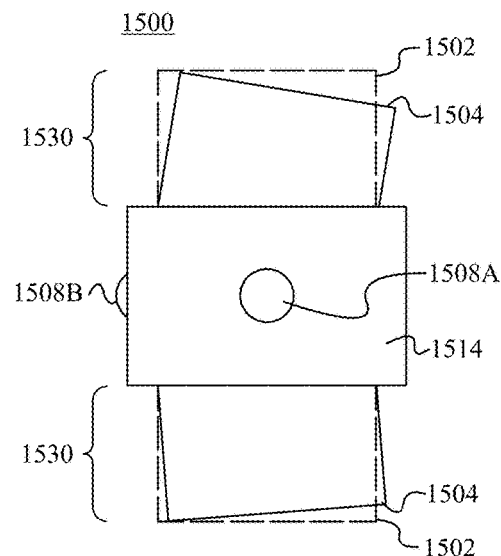
FIG. 15 illustrates a frontal view of a bone fusion device according to some embodiments.

FIG. 15 illustrates a frontal view of a bone fusion device 1500 according to some embodiments. The bone fusion device 1500 shown in FIG. 15 is substantially similar to the bone fusion device 100 except for the differences described herein. Specifically, as shown in FIG. 15, the bone fusion device 1500 comprises a frame 1514, one or more plates 1530, one or more height adjusters 1508A and one or more angle adjusters 1508B. The height adjusters 1508A are able to adjust the height or extension of the plates 1530 outside of the frame 1514 and the angle adjusters 1508B are able to adjust the angle of the top surface of the plates 1530 (with respect to the frame 1514). As a result, a user is able to dynamically adjust the position and/or orientation of the plates 1530 from a first extended and parallel position 1502, to a second extended and non-parallel position 1504. Specifically, this provides the advantage of allowing a surgeon to match both the heights and the angles needed to replace degenerated discs and/or bones. In some embodiments, the angles and/or the orientation of the angles and/or heights of each of the plates 1530 are able to be adjusted independently. Alternatively, adjustment of the angles and/or heights of one or more of the plates 1530 is dependent on the adjustment of one or more of the other plates 1530. In some embodiments, the adjustments are able to be made automatically or manually via mechanical means. Alternatively, the adjustments are able to be made automatically or manually via electrical, mechanical, hydraulic, pneumatic or other types of means well known in the art individually or in combination. In some embodiments, one or more of the height adjusters 1508A are substantially the same as the positioning components 108. Alternatively, other types of height adjusting mechanisms are able to be used as are well known in the art. In some embodiments, one or more of the height adjusters 1508A and angle adjusters 1508B are able to be combined as one or more height and angle adjusters.

For example, a plurality of height adjusters 1508A are able to independently adjust the height of a portion of the perimeter of the plates 1530 such that by raising one portion of the perimeter more or less than other portions of the perimeter, the height adjusters 1508A are able to effectuate both height, angle and orientation of the angle adjustment. Alternatively, other forms of dual height/angle adjustment mechanisms are able to be used as are well known in the art. Additionally, it should be noted that the differences to the bone fusion device 1500 described in FIG. 15 is able to be incorporated with and/or replace components of each of the other bone fusion devices described herein.

Figure 16:
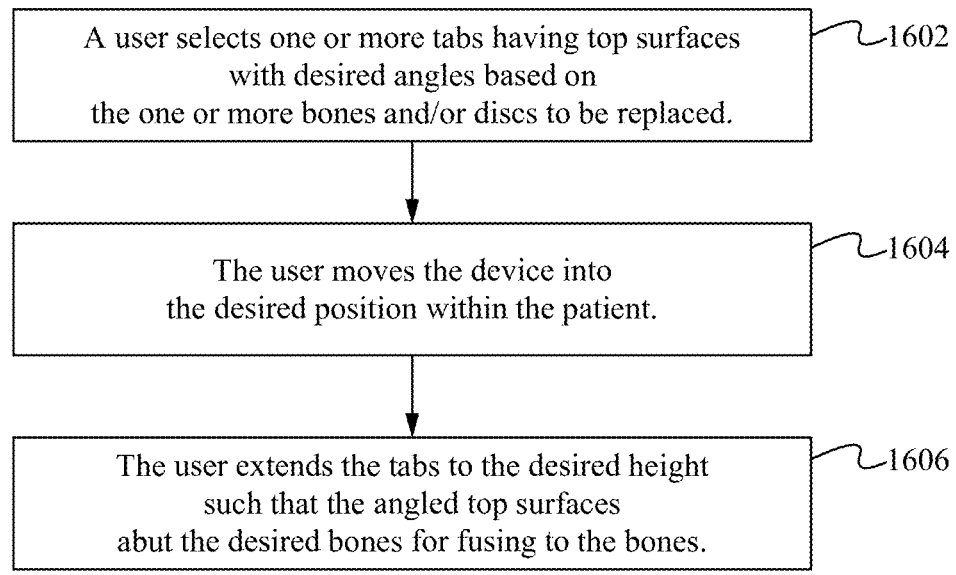
FIG. 16 illustrates a flowchart directed to a method of using the bone fusion device according to some embodiments.

A method of using the bone fusion device 1400 according to some embodiments is illustrated by the flow chart in FIG. 16. A user selects one or more plates 1430 having top surfaces 1402 with desired angles based on the one or more bones and/or discs to be replaced at the step 1602. In some embodiments, the selection comprises exchanging the current plate 1430 for another plate 1430 having a differently angled top surface 1402. The user moves the device 1400 into the desired position within the patient at the step 1604. The user extends the plates 1430 to the desired height such that the angled top surfaces 1402 abut the desired bones for fusing to the bones at the step 1606. In some embodiments, the method further comprises the user rotating the plates 1430 until the orientation of the angled top surface 1402 is as desired such that the top surfaces 1402 match and/or correct the bones and/or discs being replaced. Alternatively, the user is able to rotate the entire device 1400 until the orientation of the angled top surface 1402 matches and/or corrects the bones and/or discs being replaced. In some embodiments, the user is able to rotate the plates 1430 independent of each other. Thus, the bone fusion device 1400 is able to provide the benefit of allowing surgeons to replace one or more degenerated bones of varying heights, angles and angle orientations by adjusting the height, angle and orientation of the angle of the top surface 1402 of the plates 1430 of the device 1400. Additionally, it should be noted that one or more of the steps of the above method are able to be omitted or combined with the other methods described herein.

Figure 17:
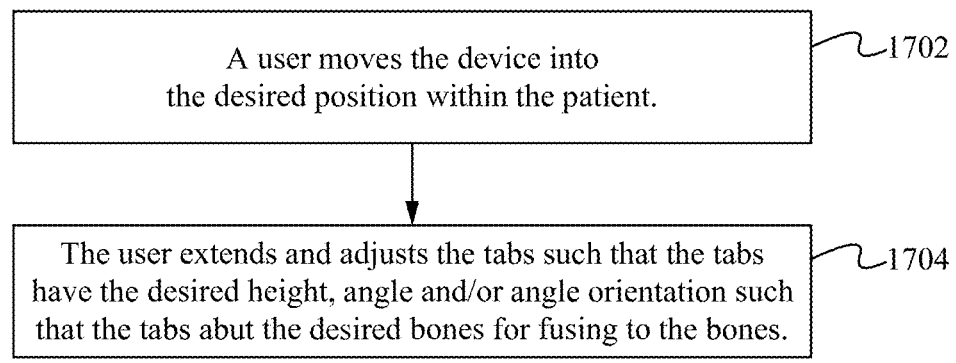
FIG. 17 illustrates a flowchart directed to a method of using the bone fusion system according to some embodiments.

A method of using the bone fusion system 1500 according to some embodiments is illustrated by the flow chart in FIG. 17. A user moves the device 1500 into the desired position within the patient at the step 1702. The user extends and adjusts the plates 1530 such that the plates 1530 have the desired height, angle and/or angle orientation such that the plates 1530 abut the desired bones for fusing to the bones at the step 1704. In some embodiments, the plates 1530 are extended and/or adjusted manually. Alternatively, the plates 1530 are able to be extended and/or adjusted automatically. In some embodiments, the plates 1530 are able to be adjusted gradually. Alternatively, the plates 1530 are adjusted to set preselected/predefined levels. Thus, the bone fusion device 1500 is able to provide the benefit of allowing surgeons to replace one or more degenerated bones of varying heights, angles and angle orientations by adjusting the height, angle and orientation of the angle of the plates 1530 of the device 1500. Additionally, it should be noted that one or more of the steps of the above method are able to be omitted or combined with the other methods described herein.

FIGS. 18A and 18B illustrate side profile views of bone fusion devices 1800 according to some embodiments. The bone fusion devices 1800 shown in FIGS. 18A and 18B are substantially similar to the bone fusion device 100 except for the differences described herein. As shown in FIGS. 18A and 18B, the bone fusion device 1800 comprises one or more plates 1830 and a frame 1814. Specifically, the plates 1830 comprise substantially non-flat top surfaces. For example, as shown in FIG. 18A, one of the plates 1830 comprise a convex top surface 1802 and the other plate 1830 comprises a concave top surface 1804. Further, as shown in FIG. 18B, the plates 1830 are able to comprise both concave and convex top surface portions 1802, 1804. In some embodiments, the concavities and/or convexities of the top surface portions 1802 are formed along a single axis (e.g. a lateral axis) such that they form one or more undulations along the single axis. Alternatively, the concavities and/or convexities of the top surface portions 1802, 1804 are able to be formed along multiple axis. In some embodiments, all of the plates 1830 share the same concavities and/or convexities of their top surface portions. Alternatively, the concavities and/or convexities of the top surface portions of the plates 1830 are able to vary for one or more of the plates 1830. In some embodiments, the plates 1830 are modular or interchangeable such that a user is able to select or replace one or more of the plates 1830 of the device 1800 with another plate 1830 based on the top surface portions of the plates 1830. Thus, the bone fusion device 1800 provides the advantage of enabling a surgeon to select plates 1830 with a top surface profile that matches and/or corrects the bones and/or discs being replaced. Additionally, it should be noted that the differences of the bone fusion devices 1800 described in FIGS. 18A and 18B are able to be incorporated with and/or replace components of each of the other bone fusion devices described herein.

A method of using the bone fusion device 1800 according to some embodiments is illustrated by the flow chart in FIG. 19. A user selects the plates 1830 of a bone fusion device 1800 based on the shape of the top surface of the plates 1830 and the shape of the surfaces to which the plates 1830 are to be fused at the step 1902. The user inserts the bone fusion device 1800 with the selected plates 1830 in between the desired bones at the step 1904. Thus, the method of using the bone fusion device 1800 provides the advantage of enabling a user to select a desired top surface of the plates 1830 of the bone fusion device 1800 based on the type of surface needed thereby increasing the effectiveness of the procedure. Additionally, it should be noted that one or more of the steps of the above method are able to be omitted or combined with the other methods described herein.

Figure 20A:
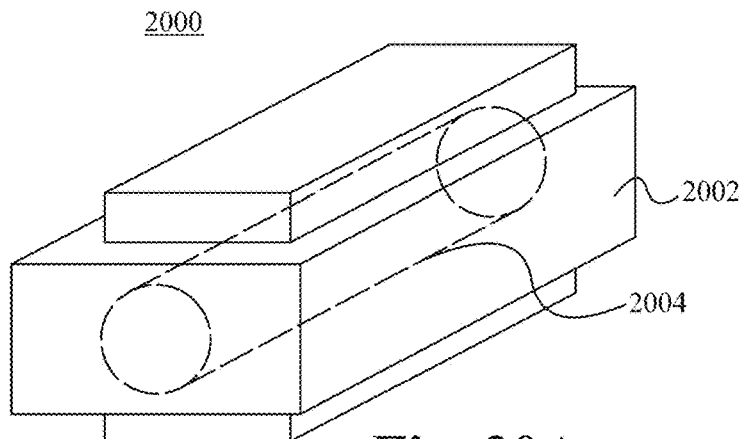
FIG. 20A illustrates a perspective view of a bone fusion system according to some embodiments.
Figure 20B:
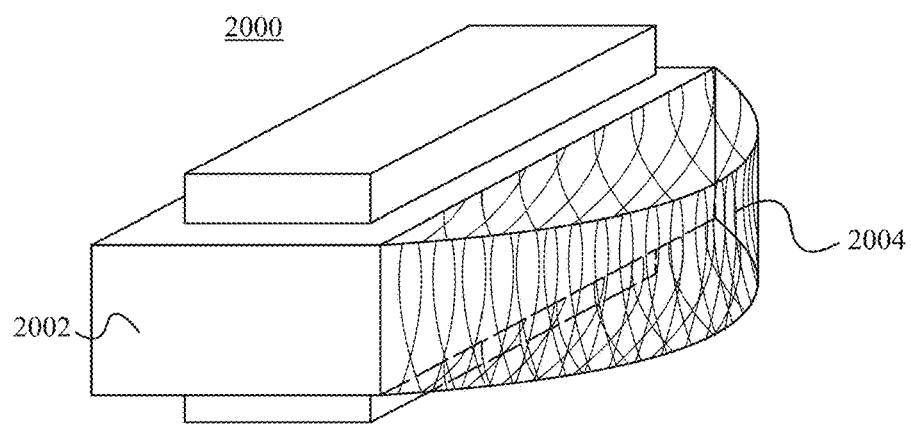
FIG. 20B illustrates a perspective view of a bone fusion system according to some embodiments.
Figure 21:
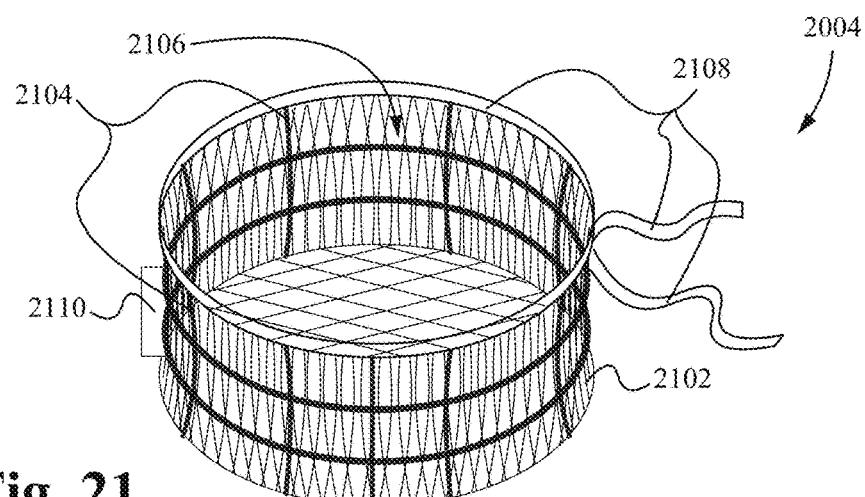
FIG. 21 illustrates a perspective view of a bone grafting material bag according to some embodiments.

FIGS. 20A and 20B illustrate perspective views of a bone fusion system 2000 according to some embodiments. The bone fusion devices 2002 shown in FIGS. 20A and 20B are substantially similar to the bone fusion device 100 except for the differences described herein. The bone fusion system 2000 comprises one or more bone fusion devices 2002 and one or more bone grafting material bags 2004. As shown in FIG. 20A, the bone grafting material bags 2004 are able to be positioned and/or coupled within the bone fusion device 2002. Additionally, as shown in FIG. 20B, the material bags 2004 are also able to be positioned or coupled outside of the bone fusion device 2002. FIG. 21 illustrates a perspective view of a bone grafting material bag 2004 according to some embodiments. As shown in FIG. 21, the material bag 2004 comprises a mesh frame 2102, one or more support bars 2104, at least one opening 2106 for filling the bag 2004 with bone graft material, one or more bag fasteners 2108 and one or more bag coupling elements 2110. In some embodiments, the support bars 2104, bag fasteners 2108 and/or bag coupling elements 2110 are able to be omitted. The support bars 2104 couple to the mesh frame 2102 in order to help the mesh frame 2102 maintain its shape. In some embodiments, the shape of the mesh frame 2102 is a cylinder (as shown in FIGS. 20A and 21). Alternatively, the shape of the mesh frame 2102 is able to be a "half-moon" prism (as shown in FIG. 20B) or other shapes capable of holding a volume of bone grafting material as are well known in the art. In some embodiments, the support bars 2104 comprise polymeric materials such that the support bars 2104 are able to maintain the shape of the material bag 2004. Alternatively, the support bars 2104 are able to comprise other materials capable of supporting the shape of the bag 2004 as are well known in the art.

The opening 2106 enables bone grating material to be packed into the bone grafting material bag 2004 and is able to vary in size based on the size of the mesh frame 2102. The bag fastener 2108 is positioned on the mesh frame 2102 such that the bag fastener 2108 is able to releasably close or fasten the opening 2106 shut such that bone grafting material within the material bag 2004 is unable to escape through the opening 2106. In some embodiments, the bag fastener 2108 comprises a hoop around the opening 2106 and a cinch cord to selectively cinch closed the opening 2106. Alternatively, the bag fasteners 2108 are able to comprise other types of fastening means as are well known in the art. In some embodiments, the material bags 2004 are able to comprise a plurality of openings 2106 and at least one bag fastener 2108 for each opening. The bag coupling element 2110 enables the material bag 2004 to be coupled to one or more bone fusion devices 2002 and/or other material bags 2004. As a result, the bone fusion system 2000 provides the advantage of enabling the user to physically pack a material bag 2004 full of bone grafting material in order to maximize the amount of grafting material provided to the bones. Further, the system 2000 provides the advantage of keeping the bone grafting material in the desired location and shape with respect to the bones to be fused to and/or the position of the bone fusion device 2002 thereby increasing the efficiency of the bone growth and/or healing process. Additionally, it should be noted that one or more of the components of the bone fusion system 2000 are able to be incorporated into the bone fusion system 1000 described above in reference to FIGS. 10-12 and vice versa.

Figure 22:
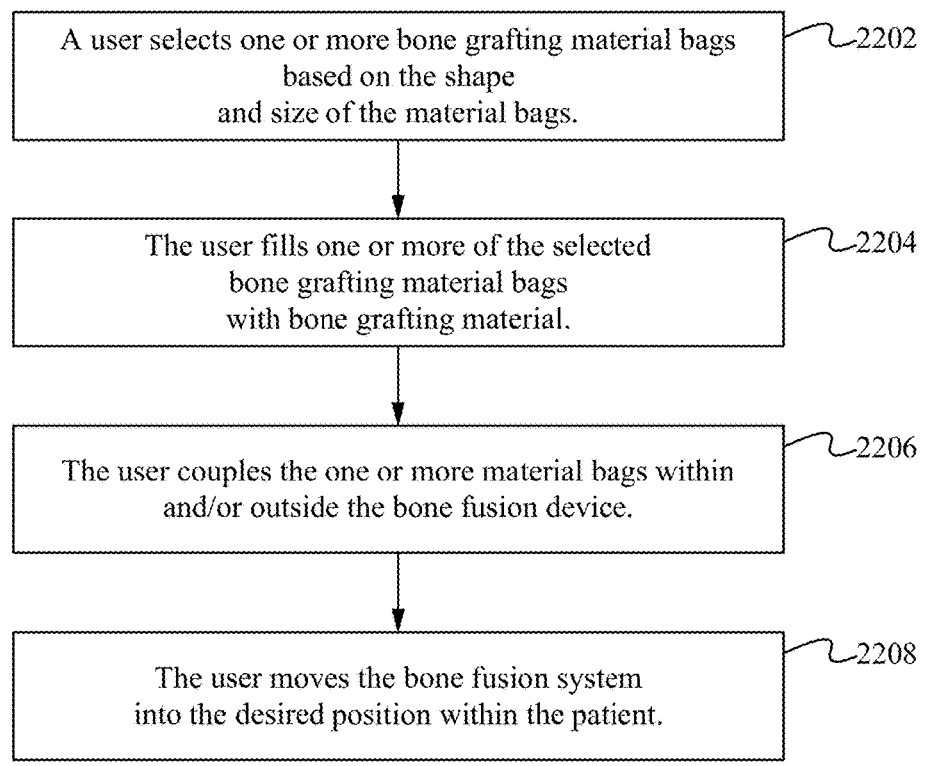
FIG. 22 illustrates a flowchart directed to a method of using the bone fusion system according to some embodiments.

A method of using the bone fusion system 2000 according to some embodiments is illustrated by the flow chart in FIG. 22. A user selects one or more bone grafting material bags 2004 based on the shape and size of the material bags 2004 at the step 2202. The user fills one or more of the selected bone grafting material bags 2004 with bone grafting material at the step 2204. In some embodiments, the material bag 2004 is filled with the bone grafting material with an implement resembling a "caulking gun." Alternatively, the material bag 2004 is able to be filled by a packing element and/or other methods of packing bone grafting material as are well known in the art. The user couples the one or more material bags 2004 within and/or outside the bone fusion device 2002 at the step 2206. The user moves the bone fusion system 2000 into the desired position within the patient at the step 2208. In some embodiments, the material bags 2004 are positioned such that they abut the bones adjacent the bone and/or disc to be replaced. Thus, the method of using the bone fusion system 2000 provides the advantage of allowing the bone grafting material to be packed into the material bags and keeping the bone grafting material in the desired position and/or shape with respect to the adjacent bones and bone fusion device 2002 such that quicker and stronger bone fusion is promoted speeding up the healing process. Additionally, it should be noted that one or more of the steps of the above method are able to be omitted or combined with the other methods described herein.

Figure 23A:
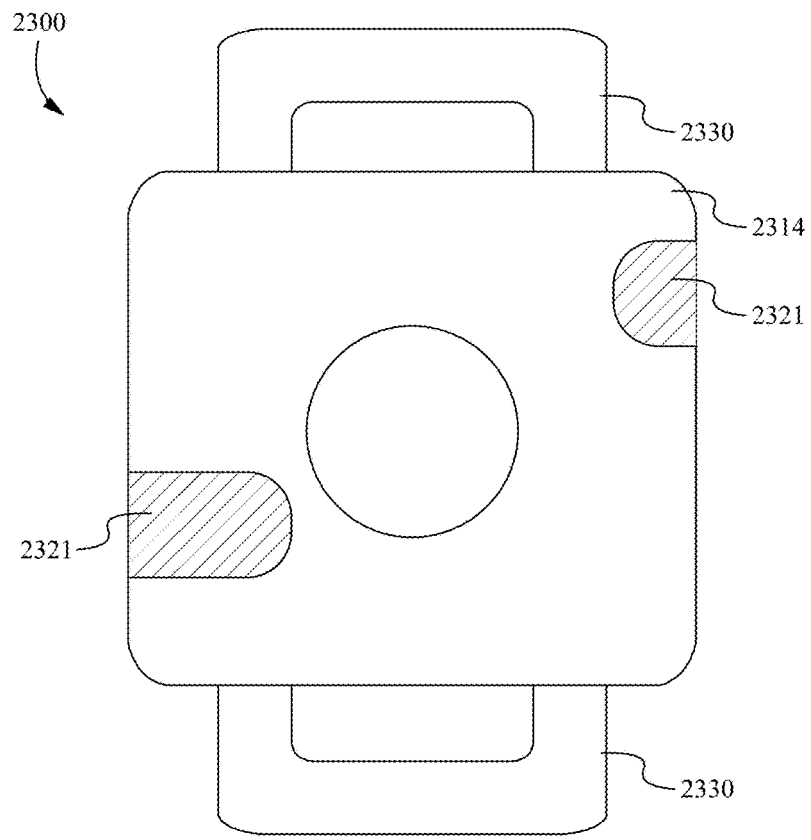
FIG. 23A illustrates a frontal view of a bone fusion device according to some embodiments.
Figure 23B:
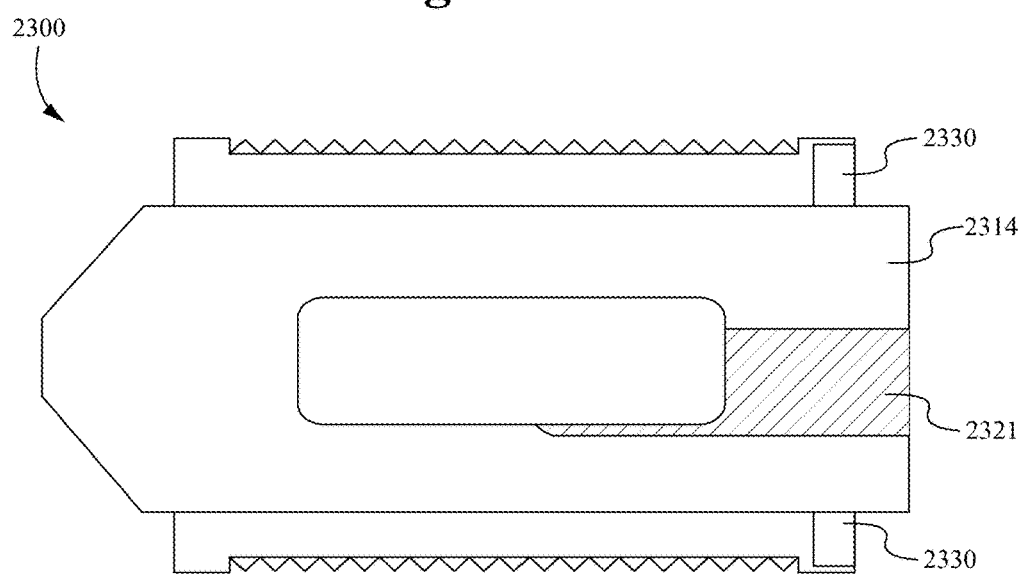
FIG. 23B illustrates a side view of a bone fusion device according to some embodiments.
Figure 23C:
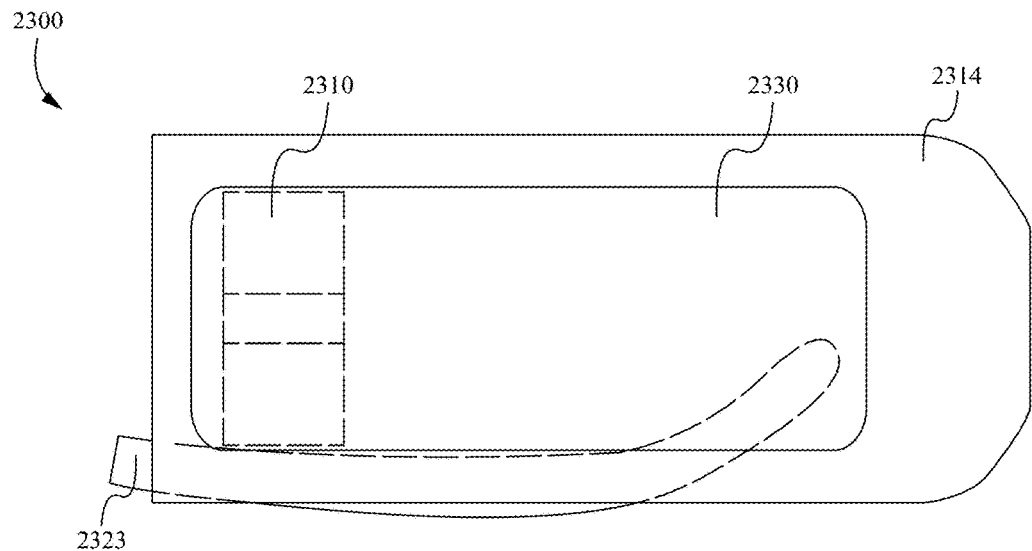
FIG. 23C illustrates a top view of an elongated member inserted within a canal of a bone fusion device according to some embodiments.

FIGS. 23A-C illustrate a front, side and top view of a bone fusion device 2300 having one or more canals according to some embodiments. The bone fusion device 2300 shown in FIGS. 23A-C is substantially similar to the bone fusion device 100 except for the differences described herein. In particular, the bone fusion device 2300 comprises a frame 2314 having one or more canals 2321, one or more tabs 2330 and extending tabs 2310. In some embodiments, the canals 2321 are positioned along the sides of the frame 2314 and a sized such that the canals 2321 are able to receive or house a portion or all of one or more elongated members 2323 (see FIG. 23D). Alternatively, one or more of the canals 2321 are able to be positioned within other portions of the frame 2314 including different angles and orientations in one or all axises of the bone fusion device 2300. Alternatively, one or more of the canals 2321 are able to be positioned within one or more of the tabs 2330. In some embodiments, the canals 2321 extend from a central area of the frame 2314 to the front or back side of the frame 2314 such that an elongated member 2323 is able to enter the canals 2321 from the front or back side of the frame 2314 (and/or the side of the frame 2314). Alternatively, one or more of the canals 2321 extend along the entire bone fusion device 2300 from the front side to the back side of the frame 2314 (or vice-versa), such that an elongated member 2323 is able to enter the canals 2321 from both or either the front or back side of the frame 2314. Alternatively, one or more of the canals 2321 are able to be housed entirely within an inner portion of the frame 2314 such that the canals 2321 breach neither the front nor the back side of the frame 2314 and the elongated members 2323 are only able to enter the canals 2321 from the side of the frame 2314.

FIG. 23C illustrates a top view of an elongated member 2323 inserted within a canal 2321 of the bone fusion device 2300 according to some embodiments. As shown in FIG. 23C, the elongated member 2323 is curved and extends from the front of the frame 2314 and canal 2321 to a central portion of the frame 2314. Alternatively, the elongated members 2323 are able to be configured such that the members 2323 extend to the front, back, or other portions of the frame 2314. In some embodiments, one or more of the elongated member 2321 are able to extend out of the canals 2321 into the central cavity of the frame 2314 and/or outside of the frame 2314. For example, the members 2323 are able to be curved or otherwise shaped such that the members 2323 enter a desired portion of the frame 2314 while not extending out of the side of the frame 2314 more than a desired distance (e.g. 1 mm). In some embodiments, the desired portion of the frame 2314 in which the members 2323 are positioned comprise between the extending blocks 2310 and the front or back side of the frame 2314 and in between the extending blocks 2310. Alternatively, the members 2323 are able to be configured such that the members 2323 are able to remain entirely within the canals 2321 and/or cavity of the frame 2314. Additionally, it should be noted that one or more of the components of the bone fusion device 2300 is able to be incorporated into the other bone fusion devices described herein.

Figure 23D:
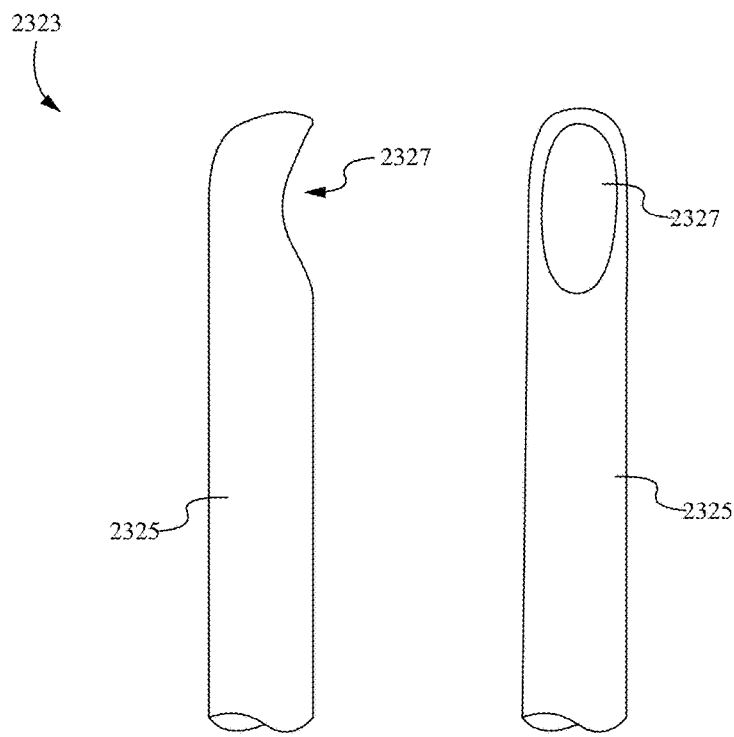
FIG. 23D illustrates a frontal and profile view of an elongated member according to some embodiments.

FIG. 23D illustrates a frontal and profile view of an elongated member 2323 according to some embodiments. As shown in FIG. 23D, the elongated member 2323 comprises a body 2325 and one or more apertures 2327. The body 2325 is sized such that the member 2323 is able to partially or wholly fit within the canals 2321. In some embodiments, the body 2325 is able to be tubular such that material is able to be inserted into the body 2325 via the apertures 2327. Alternatively, the body 2325 is able to be partially or wholly solid, wherein if the body 2325 is wholly solid the apertures 2327 are able to be omitted. Alternatively, the body 2325 is able to comprise other solid or hollow shapes as are well known in the art. As shown in FIG. 23D, the body 2325 of the elongated member 2323 is substantially straight. Alternatively, the body 2325 is able to comprise one or more curves and/or corners as are well known in the art. For example, as shown in FIG. 23C, the body 2325 is able to be curved such that the member 2323 is able to curve from the canal 2321 into the cavity of the frame 2314 of the bone fusion device 2300. In some embodiments, the elongated member 2323 is able to be bendable such that body 2325 is able to be bent to a desired shape by a user and the body 2325 will retain the desired shape. In some embodiments, the body 2325 is filled with one or more of calcium triphosphate, hydroxyapatite or other materials that are constituents of bone or promote bone growth as are well known in the art. In some embodiments, the body 2325 is able to comprise materials that are constituents of bone or promote bone growth as are well known in the art. Alternatively, the body 2325 is able to comprise the same or similar materials to that of the bone fusion device 2300. As a result, the bone fusion device 2300 and the elongated members 2323 are able to be used to position bone grafting promotive material along the device 2300 after the bone fusion device 2300 has been positioned into place within a patient. This enables the bone fusion device 2300 to ensure that the bone fusion material is not pushed out of place during the extension of the tabs 2330 or other portions of the procedure.

Figure 24:
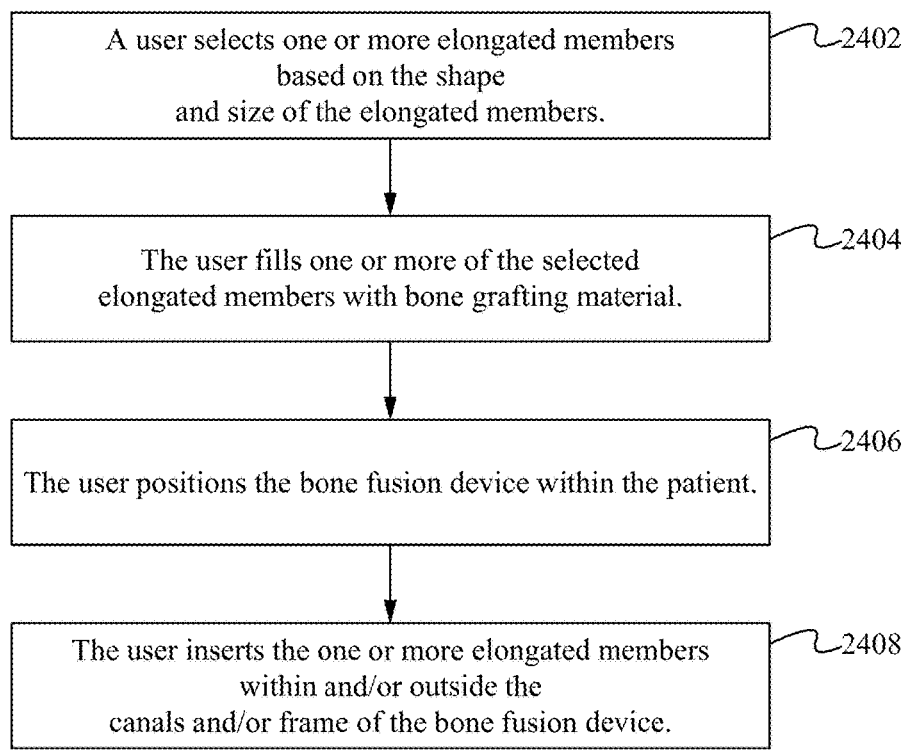
FIG. 24 illustrates a flowchart directed to a method of using the bone fusion system according to some embodiments.

A method of using the bone fusion device 2300 according to some embodiments is illustrated by the flow chart in FIG. 24. A user selects one or more elongated members 2323 based on the shape and size of the elongated members 2323 at the step 2402. Alternatively, the user selects one or more elongated members 2323 and bends them into a desired shape and size. The user fills one or more of the selected elongated members 2323 with bone grafting material at the step 2404. The user positions the bone fusion device 2300 within the patient at the step 2406. The user inserts the one or more elongated members 2323 within and/or outside the canals 2321 and/or frame 2314 of the bone fusion device 2300 at the step 2408. Alternatively, one or more of the elongated members 2323 are able to be positioned within and/or outside of the canals 2321 before or during the positioning of the bone fusion device 2300 within the patient. Thus, the method of using the bone fusion system 2300 provides the advantage of allowing the bone grafting material to be packed into the elongated members 2323 and positioned after the positioning of the bone fusion device 2300 within the patient. As a result, the bone fusion device 2300 is able to prevent the elongated members 2323 from being moved during the positioning of the bone fusion device within the patient thereby keeping the bone grafting material in the desired position and/or shape with respect to the adjacent bones and bone fusion device 2300 such that quicker and stronger bone fusion is promoted speeding up the healing process. Additionally, it should be noted that one or more of the steps of the above method are able to be omitted or combined with the other methods described herein.

Figure 25:
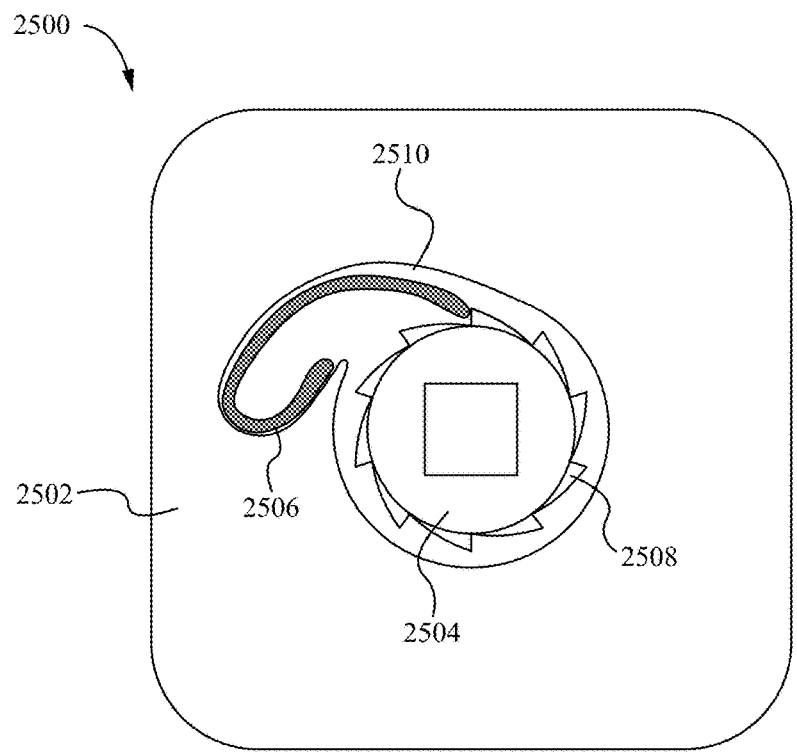
FIG. 25 illustrates a bone fusion device having a ratchet mechanism according to some embodiments.

FIG. 25 illustrates a bone fusion device 2500 having a ratchet mechanism according to some embodiments. The bone fusion device 2500 shown in FIG. 25 is able to be substantially similar to the other bone fusion devices except for the differences described herein. In particular, the bone fusion device 2500 comprises a body 2502, a positioning means 2504 and a ratchet mechanism including a pawl 2506 and one or more gear teeth 2508 on the perimeter of the positioning means 2504. As shown in FIG. 25, the pawl 2506 is positioned within a cavity 2510 of the body 2502 that is adjacent to the positioning means 2504 such that the arm of the pawl 2506 is able to abut or be in communication with the one or more gear teeth 2508. As a result, the pawl 2506 is able to permit the positioning means 2504 to rotate in one direction while preventing the positioning means 2504 from rotating back in the opposite direction. Specifically, the size and/or angles of the gear teeth 2508 are able to be adjusted such that as the positioning means 2504 rotate in a first direction the pawl 2506 is able to slide over the gear teeth 2508 due to the angle of the pawl 2506 and/or the angle of a first side of the gear teeth 2508. Contrarily, if the positioning means 2504 starts to rotate in a second or opposite direction the pawl 2506 is unable to slide over the gear teeth 2508 due to the angle of the pawl 2506 and/or the angle of a second or opposite side of the gear teeth 2508 thereby stopping or preventing the rotation of the positioning means in the second or opposite direction. As a result, the bone fusion device 2500 having a ratchet mechanism provides the benefit of ensuring that the tabs stay in place when extended because the ratchet mechanism prevents them from retracting.

In some embodiments, the ratchet mechanism comprises a release mechanism (not shown) that when activated separates or changes the dynamic of the pawl 2506 and the gear teeth 2508 such that the positioning means 2504 is able to rotate in the second or opposite direction without being stopped by the pawl 2506. Alternatively, the angle of the pawl 2506 and/or gear teeth 2508 of the ratchet mechanism are able to be configured such that with a desired force F the positioning means 2504 is able to be rotated in the second or opposite direction despite the presence of the pawl 2506. In particular, the desired force F is able to be greater than the maximum force that would occur on the tabs within a patient after implantation such that the rotation in the second direction would only occur if the surgeon needed to rotate the positioning means 2504 in that direction. In some embodiments, the pawl 2506 comprises nitinol or stainless steel. Alternatively, the pawl 2506 is able to comprise other types of suitable materials as are well known in the art. In some embodiments, the first direction of rotation corresponds to the direction required to extend the tabs of the device 2500 and the second direction corresponds to the direction required to retract the tabs of the device. Alternatively, the first direction is able to correspond to the direction required to retract the tabs of the device 2500 and the second direction corresponds to the direction required to extend the tabs of the device.

Figure 26A:
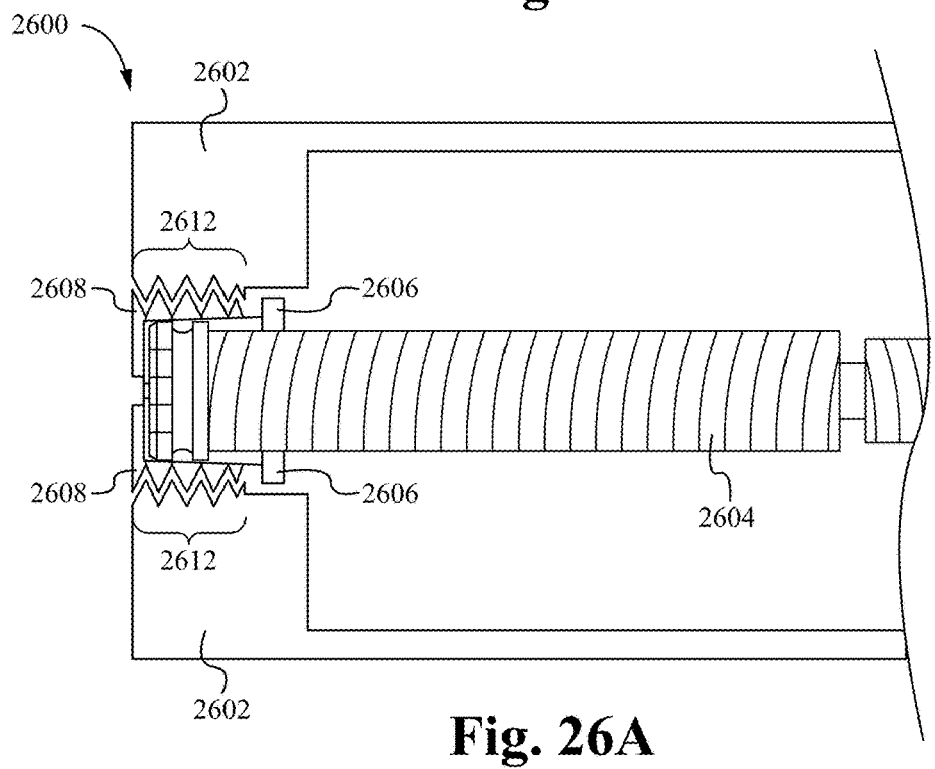
FIG. 26A illustrates a cross sectional view of a bone fusion device having a lock mechanism according to some embodiments.
Figure 26B:
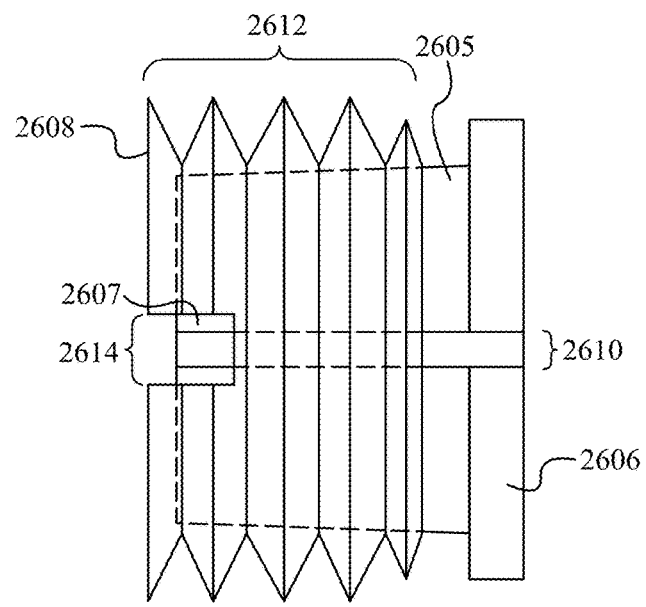
FIG. 26B illustrates a side view of a lock mechanism according to some embodiments

FIG. 26A illustrates a cross sectional view of a bone fusion device 2600 having a lock mechanism according to some embodiments. The bone fusion device 2600 shown in FIG. 26A is able to be substantially similar to the other bone fusion devices except for the differences described herein. In particular, the bone fusion device 2600 comprises a body 2602, a positioning means 2604 and a lock mechanism including a collar 2606 and a choke 2608. As shown in FIG. 26B, the collar 2606 has a thick end 2605, a narrow end 2607 and a gap 2610 and the choke 2608 is configured to fit around the narrow end 2607 of the collar 2606. As a result, if the choke 2608 is pushed or otherwise forced down on the collar 2606 towards the thick end 2605, it causes the gap 2610 of the collar 2606 to contract thereby continually reducing the circumference of the collar 2606 as it moves until the gap 2610 is gone. Similarly, if the choke 2608 is moved back toward the narrow end 2607 of the collar 2606, the gap 2610 is able to continually increase up to its original size increasing the circumference of the collar 2606 as permitted by the inner circumference of the choke 2608. As shown in FIG. 26A, the lock mechanism 2606, 2608 is positioned around the end of the positioning means 2604 within an aperture at an end of the body 2602. As a result, when the choke 2608 causes the circumference of the collar 2606 to reduce, it causes the collar 2606 to provide a choking force on the positioning means 2604 such that the positioning means 2604 are unable to rotate due to the friction between the collar 2606 and the surface of the positioning means 2604. As a result, the lock mechanism is able to provide the benefit of enabling the positioning means and thus the tabs to be locked in place thereby reducing the risk of the tabs undesirably retracting.

In some embodiments, the choke 2608 has threading 2612 that corresponds to threading of the body 2602 such that if the choke 2608 is rotated the threading 2612 causes the choke 2608 to move further in or out of the aperture of the body 2602 and thereby move with respect to the collar 2606 in order to lock or unlock the positioning means 2604 as described above. In such embodiments, the choke 2608 is able to have one or more cutouts 2614 for receiving a tool for rotating the choke 2608. Alternatively, the threading 2612 is able to act as "snap-fit" stops or ridges/valleys that correspond to ridges/valleys of the body 2602 such that if the choke 2608 is pushed further into the aperture of the body 2602 and toward the thick end 2605 of the collar 2606, the ridges of the threading 2612 compress and then spring/snap into the valleys of the body 2602 thereby preventing the choke 2608 from being forced back away from end thick end 2605 of the collar 2606. In some embodiments, the thickness of the collar 2606 gradually changes from the narrow end 2607 to the thick end 2605. Alternatively, the thickness of the collar 2606 is able to change in one or more increments. For example, the thickness is able to remain substantially constant until the next increment is reached.

Figure 27A:
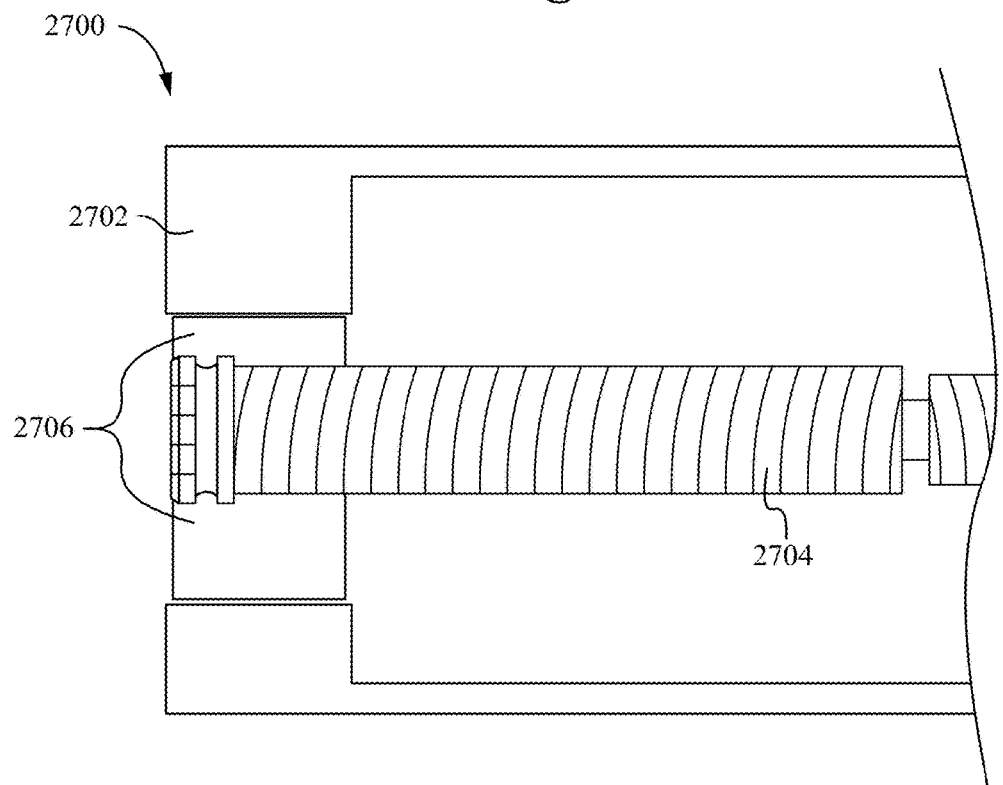
FIG. 27A illustrates a side cross sectional view of a bone fusion device having an oblong locking mechanism according to some embodiments.
Figure 27B:
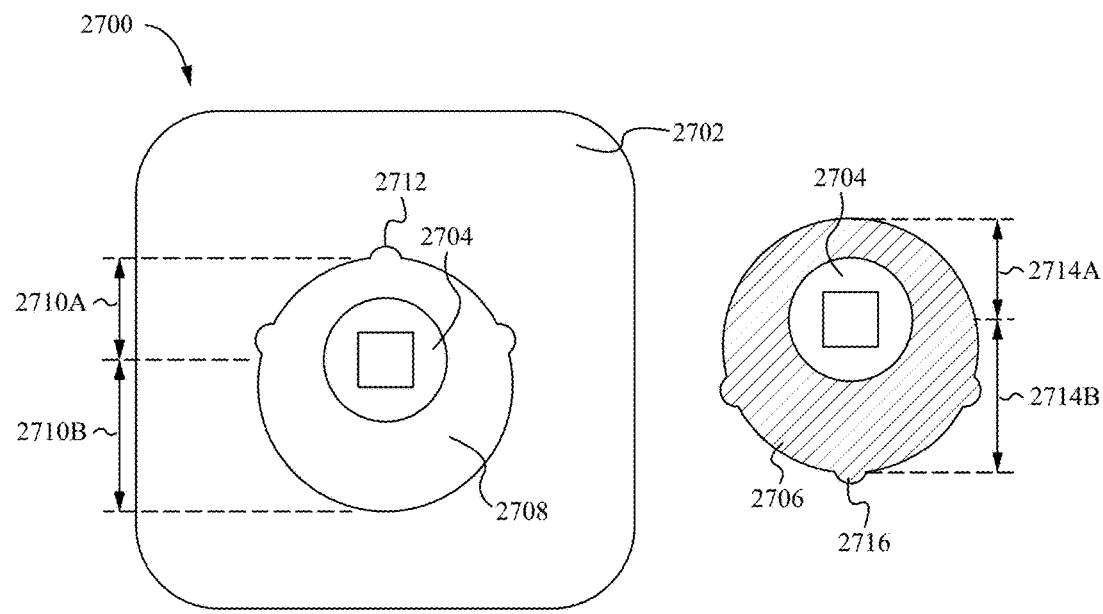
FIG. 27B illustrates a frontal view of a body of the bone fusion device and the oblong locking mechanism according to some embodiments.

FIGS. 27A-F illustrate a bone fusion device 2700 having an oblong lock mechanism according to some embodiments. The bone fusion device 2700 shown in FIGS. 27A-F is able to be substantially similar to the other bone fusion devices except for the differences described herein. As shown in FIGS. 27A and 27B, which illustrate side cross sectional and frontal views respectively, the bone fusion device 2700 comprises a body 2702, positioning means 2704 within the body 2603 and an oblong locking member 2706 surrounding one end of the positioning means 2704 and having one or more bumps 2716. The body 2702 comprises an aperture 2708 for receiving the positioning means 2704 and the locking member 2706, wherein the aperture 2708 includes one or more notches 2712 that are able to selectively receive the one or more bumps 2716. In particular, as shown in FIG. 27B, the aperture 2708 is oblong such that it has a short side 2710A and a long side 2710B that correspond to a short side 2714A and long side 2714B of the oblong locking member 2706.

Figure 27C:
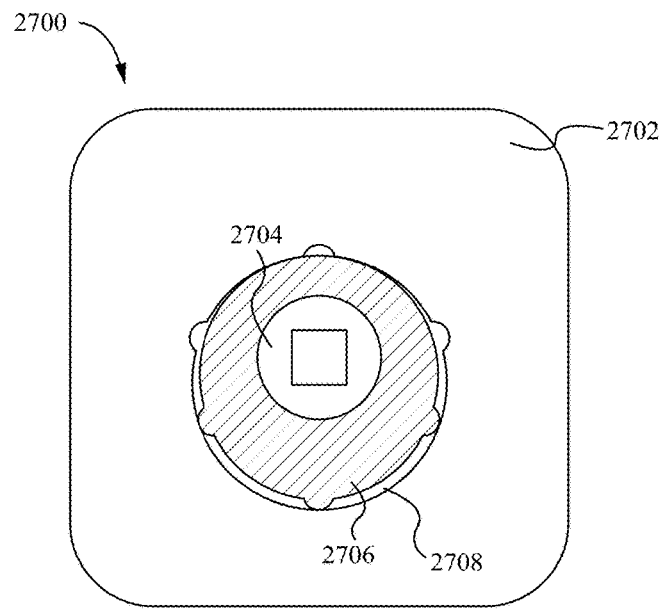
FIG. 27C illustrates a frontal view of a bone fusion device having an oblong locking mechanism in the unlocked position according to some embodiments.
Figure 27D:
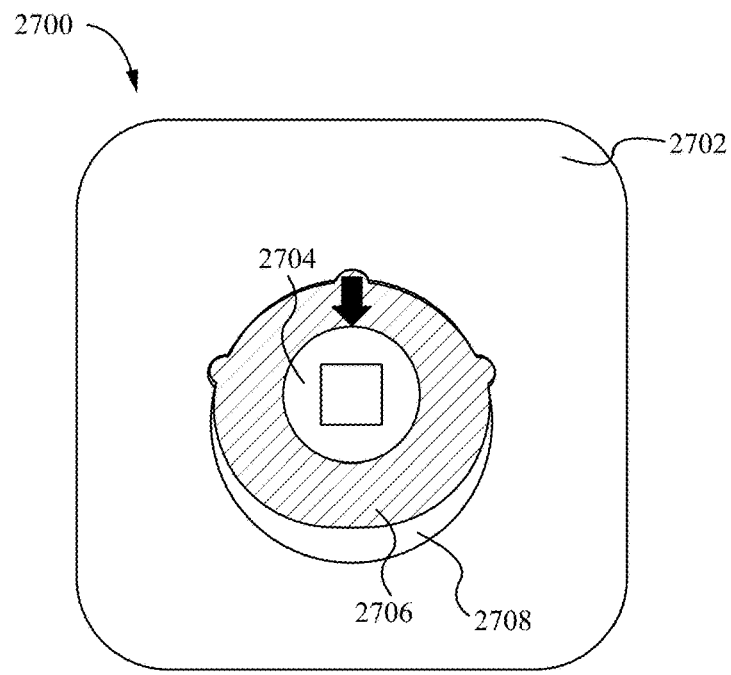
FIG. 27D illustrates a frontal view of a bone fusion device having an oblong locking mechanism in the locked position according to some embodiments.

As a result, as shown in FIG. 27D, the oblong locking member 2706 is able to be rotated into a "locked" position where the short side 2714A of the locking member 2706 is positioned within the long side 2710B of the aperture 2708 and the long side 2714B of the locking member 2706 is positioned within the short side 2710A of the aperture 2708. In this locked position, the positioning means 2704 will be unable to rotate freely as pressure is applied to the positioning means 2704 by the long side 2714B of the locking member 2706 in the direction indicated by the arrow because the long side 2714B is under compression by the short side 2710A of the aperture 2708. In particular, the force applied to the positioning means 2704 by the locking member 2706 in the locked position increases the friction between the positioning means 2704 and the locking member 2706 such that the positioning means 2704 is unable to rotate. In contrast, as shown in FIG. 27C, the oblong locking member 2706 is able to be rotated into an "unlocked" position where the short side 2714A of the locking member 2706 is positioned within the short side 2710A of the aperture 2708 and the long side 2714B of the locking member 2706 is positioned within the long side 2710B of the aperture 2708. In this "unlocked" position, the positioning means 2704 will be able to rotate freely as little or no pressure is applied to the positioning means 2704 by the locking member 2706 because the locking member 2706 is not under compression by the aperture 2708. As a result, the lock mechanism is able to provide the benefit of enabling the positioning means and thus the tabs to be locked in place thereby reducing the risk of the tabs undesirably retracting.

In some embodiments, the oblong locking member 2706 comprises PEEK. Alternatively, the oblong locking member 2706 is able to comprise other types of biocompatable materials that are flexible such that they are able to be compressed and apply a stopping force to the positioning means 2704. In some embodiments, the notches 2712 and the bumps 2716 are configured such that one or more of the bumps 2716 slide into the notches 2712 when the oblong locking member 2706 is in either the locked or unlocked positions. In particular, in such embodiments the bumps 2716 and notches 2712 are able to provide an indication that the locking member 2706 has been fully rotated in the locked or unlocked position as well as preventing the oblong locking member 2706 from slipping out of the locked or unlocked position. In some embodiments, the oblong locking member 2706 comprising one or more apertures that facilitate the rotation of the locking member 2706 by a tool or user.

Figure 27E:
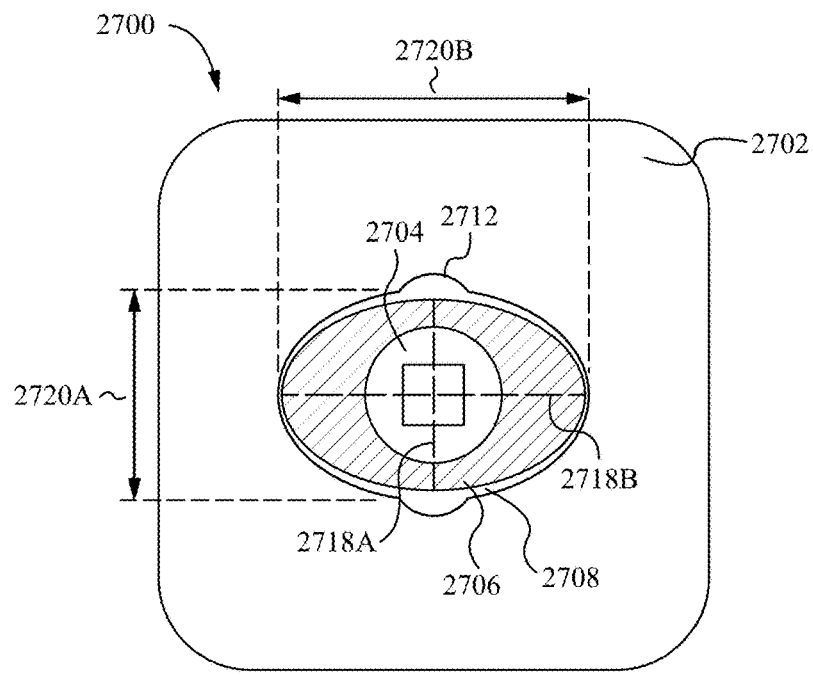
FIG. 27E illustrates a frontal view of a bone fusion device having an oblong locking mechanism in the unlocked position according to some embodiments.
Figure 27F:
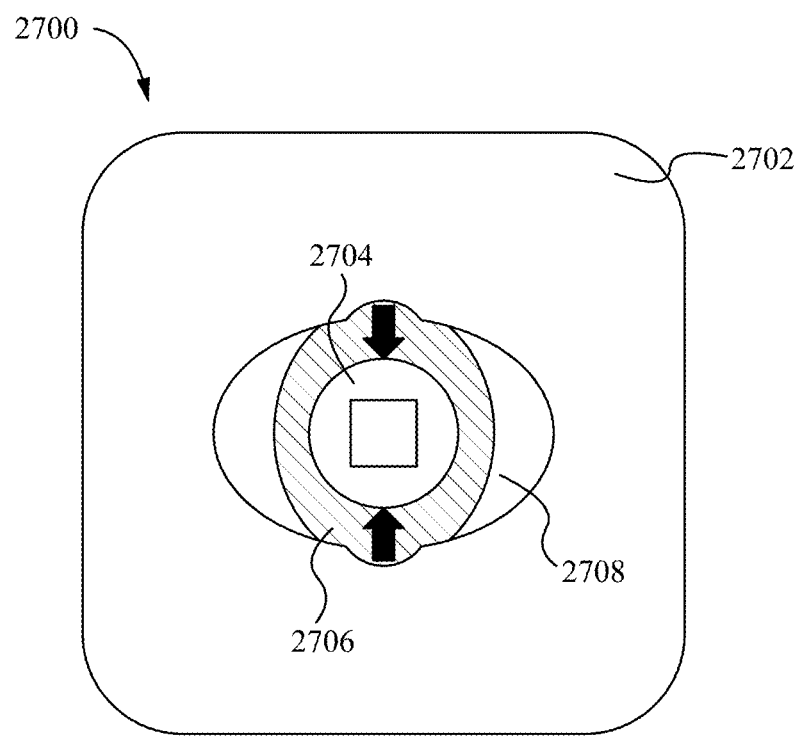
FIG. 27F illustrates a frontal view of a bone fusion device having an oblong locking mechanism in the locked position according to some embodiments.

FIGS. 27E and 27F illustrate an alternate embodiment of the bone fusion device 2700 having the oblong locking mechanism according to some embodiments. In particular, as shown in FIGS. 27E and 27F, the aperture 2708 and the oblong locking member 2706 are ovular such that they each have a short dimension 2718A, 2720A and a long dimension 2718B, 2720B. As a result, when rotated into a "locked" position as shown in FIG. 27F, the positioning means 2704 is unable to rotate freely as pressure is applied to the positioning means 2704 from both sides along the long dimension 2718B of the locking member 2706 in the direction indicated by the arrows because the long dimension 2718B is under compression by the short dimension 2720A of the aperture 2708. In contrast, as shown in FIG. 27E, the oblong locking member 2706 is able to be rotated into an "unlocked" position where the short dimension 2718A of the locking member 2706 is positioned within the short dimension 2720A of the aperture 2708 and the long dimension 2718B of the locking member 2706 is positioned within the long dimension 2720B of the aperture 2708. Like in FIG. 27C, in this "unlocked" position the positioning means 2704 will be able to rotate freely as little or no pressure is applied to the positioning means 2704 by the locking member 2706 because the locking member 2706 is not under compression by the aperture 2708. In some embodiments, the aperture 2708 comprises one or more notches 2712 that are configured such that ends of the long dimension 2718B slide into the notches 2712 when the oblong locking member 2706 is in the locked positions. In particular, in such embodiments the notches 2712 are able to provide an indication that the locking member 2706 has been fully rotated in the locked or unlocked position as well as preventing the oblong locking member 2706 from slipping out of the locked or unlocked position. Alternatively, the oblong locking member 2706 is able to comprise on or more bumps 2716 for sliding into the notches 2712 in addition to or in lieu of the ends of the long dimension 2718B. As a result, the lock mechanism is able to provide the benefit of enabling the positioning means and thus the tabs to be locked in place thereby reducing the risk of the tabs undesirably retracting.

Thus, the bone fusion device, system and method described herein has numerous advantages. First, the bone fusion device, system and method provide the advantage of substantially matching the device profiles with the horizontal profiles of the bones to be fused, thereby increasing the strength and efficiency of the fusion process. As a result, the bone fusion device does not need to be turned to be in the proper orientation between the bones of the patient whether the procedure is anterior, posterior, lateral or transforaminal lumbar interbody fusion. Second, the bone fusion device, system and method provide the advantage of allowing the plates to be extended from angles other than parallel to the screws and/or the elongated dimension of the devices, which is critical in procedures where the device is to be inserted from varying angles. Further, the bone fusion device, system and method provides the advantage of enabling multiple bone fusion devices to be coupled together via a replacement body in order to replace a degenerated bone and the adjacent discs. Further, the lock mechanism is able to provide the benefit of enabling the positioning means and thus the tabs to be locked in place thereby reducing the risk of the tabs undesirably retracting. Additionally, the bone fusion device, system and method provides the advantage of enabling the angle and orientation of the plates to be adjusted to correct scoliosis an other spine/bone angle irregularities. Also, the bone fusion device, system and method provides the advantage of enabling a surgeon to select plates with a top surface profile that matches and/or corrects the bones and/or discs being replaced. Moreover, the bone fusion device, system and method provides the advantage of enabling the user to physically pack a material bag full of bone grafting material in order to maximize the amount of grafting material provided to the bones, as well as providing the advantage of keeping the bone grafting material in the desired location and shape with respect to the bones to be fused to and/or the position of the bone fusion device thereby increasing the efficiency of the bone growth and/or healing process. Finally, the bone fusion device, system and method provides the advantage of allowing the bone grafting material to be packed into differently sized elongated members that are able to be positioned partially or wholly within the bone fusion devices thereby keeping the bone grafting material in the desired position and/or shape with respect to the adjacent bones.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention. For example, it should be noted that although the above bone fusion devices are described in reference to a pair of extending blocks, a pair of screws, and wherein each plate is shaped such that the ends are larger than the middle, and the size of the plate gradually increases while going from the middle to the ends, the use of a single extending block in the above embodiments is contemplated. Specifically, if using a single extending block, the above embodiments would operate the same except the positioning components would comprise a single screw that when engaged would cause the single extending block to move from one end of the screw to the other end thereby exerting a force against the plates such that they move into the extended position. In such embodiments, each plate is shaped such that one end is larger than the opposite end, and the size of the plate gradually increases going from the smaller end to the larger end.

What is claimed is:

1. A bone fusion device for insertion into a desired location comprising:
   a. a body having a first end and an interior cavity;
   b. one or more tabs each having an external surface, an internal surface and a support rib along a length of the internal surface, wherein the one or more tabs are configured to selectively move from a retracted position within the body to an extended position extending out of the body and further wherein the support rib of each of the tabs has a uniform width and extends vertically from less than an entire width of the internal surface of the respective tab within the interior cavity at a center of a width of the tab; and
   c. one or more extending blocks configured to slide along a path within the body in order to move the one or more tabs between the retracted position and the extended position, each of the one or more extending blocks comprising an external surface configured to abut a portion of the internal surface of the respective tab, wherein the one or more extending blocks each have a rib slot comprising an opening in the external surface of the extending block, wherein generally parallel sides of the rib slot extend away from the external surface of the extending block and each meet a bottom surface of the rib slot, wherein a distance between the sides of the rib slot is uniform within the rib slot from the external surface of the extending block to the bottom surface, to surround the uniform width of the respective support rib;

wherein an angle formed by the portion of the internal surface of the respective tab that abuts the external surface of the respective block with respect to the path is incongruent with an angle formed by an internally facing surface of the support rib that faces the bottom surface of the respective rib slot with respect to the path.

2. The device of claim 1, wherein the external surface of the one or more tabs comprises a plurality of teeth such that the external surface is serrated.

3. The device of claim 1, wherein the body comprises an exterior surface having one or more surface channels.

4. The device of claim 3, wherein each of the one or more surface channels comprises a gripping aperture for receiving a fingertip of a finger of a gripping apparatus positioned within the one or more surface channels.

5. The device of claim 3, further comprising a positioning element having a positioning aperture and mechanically coupled with the one or more extending blocks such that moving the positioning element causes the one or more extending blocks to slide within the body.

6. The device of claim 5, wherein the one or more surface channels are positioned along the exterior surface on a plane perpendicular to a plane surface in which the positioning aperture of the positioning element is disposed such that fingers of a gripping apparatus are able to enter the one or more surface channels by moving parallel to the plane.

7. The device of claim 1, wherein the body of the bone fusion device has a height of less than or equal to 5 mm.

8. The device of claim 7, wherein the one or more tabs consist of a single tab.

9. The device of claim 1, wherein the body has a top view profile selected from the group consisting of oval, kidney shaped, round and banana shaped.

10. The device of claim 1, wherein one or more of the one or more tabs have a top view profile selected from the group consisting of oval, kidney shaped, round and banana shaped.

11. The device of claim 1, wherein the one or more tabs have a top view profile with the same shape as a top view profile of the body.

12. The device of claim 1, wherein the external surface of the one or more tabs is non-planar.

13. The device of claim 1, wherein the external surface of the one or more tabs is convex or concave.

14. The device of claim 1, wherein the one or more tabs are modular and detachably coupled to the body such that a tab is able to be selectively removed and replaced by another tab.

15. The device of claim 1, further comprising one or more bone graft bags coupled to the body for holding bone graft material.

16. The device of claim 15, wherein the one or more bone graft bags are coupled to the exterior of the body.

17. The device of claim 15, wherein the one or more bone graft bags are positioned within the interior cavity.

18. The device of claim 15, wherein the one or more bone graft bags comprise a mesh frame having one or more support bars such that the one or more bone graft bags are not flaccid.

19. The device of claim 15, wherein the one or more bone graft bags comprise one or more openings for inserting bone graft material and a bag fastener configured to close the one or more openings.

20. The device of claim 15, wherein the one or more bone graft bags have a cylindrical shape.

21. A bone fusion assembly for insertion into a desired location, the bone fusion assembly comprising:
 a. a body having a front end, a back end opposite the front end, an interior cavity, an exterior surface and one or more canals positioned along the exterior surface;
 b. one or more hollow members positioned at least partially within the one or more canals;
 c. one or more tabs configured to selectively move between a retracted position within the interior cavity and an extended position extending out of the body in order to brace the bone fusion assembly in the desired location, each of the one or more tabs comprising a first tab end proximate the front end and a second tab end proximate the back end, each of the one or more tabs further comprising a support rib having a uniform width and continuously extending vertically from the first tab end to the second tab end within the interior cavity, extending from less than an entire width of the respective tab at a center of the width of the respective tab;
 d. a positioning element positioned within the interior cavity and accessible from exterior to the body through the front end; and
 e. a plurality of extending blocks coupled with the positioning element and in contact with the one or more tabs such that moving the positioning element causes the plurality of extending blocks to slide along a path within the body in order to move the one or more tabs between the extended position and the retracted position, each of the plurality of extending blocks comprising an external surface configured to abut a portion of an internal surface of the respective tab, wherein the plurality of extending blocks each have a rib slot comprising an opening in the external surface of the extending block, wherein generally parallel sides of the rib slot extend away from the external surface of the extending block and each meet a bottom surface of the rib slot, wherein a distance between the sides of the rib slot is uniform within the rib slot from the external surface of the extending block to the bottom surface, to surround the uniform width of the respective support rib;

wherein an angle formed by the portion of the internal surface of the respective tab that abuts the external surface of the respective block with respect to the path is incongruent with an angle formed by an internally facing surface of the support rib that faces the bottom surface of the respective rib slot with respect to the path.

22. The assembly of claim 21, wherein the one or more canals are accessible from the front end and extend through a plane perpendicular to the front end.

23. The assembly of claim 22, wherein the one or more canals extend from the exterior surface to the interior cavity.

24. The assembly of claim 23, wherein the one or more hollow members comprise one or more apertures and are filled with bone grafting material.

25. The assembly of claim 24, wherein at least one of the one or more hollow members is curved and extends from within one of the one or more canals into the interior cavity of the body.

26. A bone fusion device for insertion into a desired location comprising:
 a. a body having a first end, a second end and an interior cavity;
 b. one or more tabs each having an external surface, an internal surface and a support rib having a uniform width and extending vertically along the internal surface from proximate the first end to proximate the second end within the interior cavity, extending from less than an entire width of the internal surface of the respective tab at a center of a width of the respective tab, wherein the one or more tabs are configured to selectively move from a retracted position within the body to an extended position extending out of the body; and
 c. one or more extending blocks configured to slide along a path within the body in order to move the one or more tabs between the retracted position and the extended position, each of the one or more extending blocks comprising an external surface configured to abut a portion of the internal surface of the respective tab, wherein the one or more extending blocks each have a rib slot comprising an opening in the external surface of the extending block, wherein generally parallel sides of the rib slot extend away from the external surface of the extending block and each meet a bottom surface of the rib slot, wherein a distance between the sides of the rib slot is uniform within the rib slot from the external surface of the extending block to the bottom surface, to surround the uniform width of the respective support rib;

wherein an angle formed by the portion of the internal surface of the respective tab that abuts the external surface of the respective block with respect to the path is incongruent with an angle formed by an internally facing surface of the support rib that faces the bottom surface of the respective rib slot with respect to the path.

27. A bone fusion device for insertion into a desired location comprising:
   a. a body having a first end and an interior cavity;
   b. one or more tabs each having an external surface, an internal surface and a support rib along a length of the internal surface, wherein the one or more tabs are configured to selectively move from a retracted position within the body to an extended position extending out of the body and further wherein the support rib of each of the tabs extends vertically from less than an entire width of the internal surface of the respective tab within the interior cavity at a center of a width of the tab, wherein a vertical height of the support rib is less at a center point of the respective tab than at an end of the respective tab, wherein the external surface of the one or more tabs comprises a plurality of teeth such that the external surface is serrated; and
   c. one or more extending blocks configured to slide along a path within the body in order to move the one or more tabs between the retracted position and the extended position, each of the one or more extending blocks comprising an external surface configured to abut a portion of the internal surface of the respective tab, wherein the one or more extending blocks each have a rib slot comprising an opening in the external surface of the extending block, wherein generally parallel sides of the rib slot extend away from the external surface of the extending block and each meet a bottom surface of the rib slot, wherein a distance between the sides of the rib slot is uniform within the rib slot from the external surface of the extending block to the bottom surface, to surround a uniform width of the respective support rib;

wherein an angle formed by the portion of the internal surface of the respective tab that abuts the external surface of the respective block with respect to the path is incongruent with an angle formed by an internally facing surface of the support rib that faces the bottom surface of the respective rib slot with respect to the path.

28. A bone fusion assembly for insertion into a desired location, the bone fusion assembly comprising:
   a. a body having a front end, a back end opposite the front end, an interior cavity, an exterior surface and one or more canals positioned along the exterior surface;
   b. one or more hollow members positioned at least partially within the one or more canals;
   c. one or more tabs configured to selectively move between a retracted position within the interior cavity and an extended position extending out of the body in order to brace the bone fusion assembly in the desired location, each of the one or more tabs comprising a first tab end proximate the front end and a second tab end proximate the back end, each of the one or more tabs further comprising a support rib that continuously extends vertically from the first tab end to the second tab end within the interior cavity, extending from less than an entire width of the respective tab at a center of the width of the respective tab, wherein a vertical height of the support rib is less at a center point of the respective tab than at an end of the respective tab, wherein the external surface of the one or more tabs comprises a plurality of teeth such that the external surface is serrated;
   d. a positioning element positioned within the interior cavity and accessible from exterior to the body through the front end; and
   e. a plurality of extending blocks coupled with the positioning element and in contact with the one or more tabs such that moving the positioning element causes the plurality of extending blocks to slide along a path within the body in order to move the one or more tabs between the extended position and the retracted position, each of the plurality of extending blocks comprising an external surface configured to abut a portion of an internal surface of the respective tab, wherein the plurality of extending blocks each have a rib slot comprising an opening in the external surface of the extending block, wherein generally parallel sides of the rib slot extend away from the external surface of the extending block and each meet a bottom surface of the rib slot, wherein a distance between the sides of the rib slot is uniform within the rib slot from the external surface of the extending block to the bottom surface, to surround the uniform width of the respective support rib;

wherein an angle formed by the portion of the internal surface of the respective tab that abuts the external surface of the respective block with respect to the path is incongruent with an angle formed by an internally facing surface of the support rib that faces the bottom surface of the respective rib slot with respect to the path.

29. A bone fusion device for insertion into a desired location comprising:
   a. a body having a first end, a second end and an interior cavity;
   b. one or more tabs each having an external surface, an internal surface and a support rib extending vertically along the internal surface from proximate the first end to proximate the second end within the interior cavity, extending from less than an entire width of the internal surface of the respective tab at a center of a width of the respective tab, wherein the one or more tabs are configured to selectively move from a retracted position within the body to an extended position extending out of the body, wherein a vertical height of the support rib is less at a center point of the respective tab than at an end of the respective tab, wherein the external surface of the one or more tabs comprises a plurality of teeth such that the external surface is serrated; and
   c. one or more extending blocks configured to slide along a path within the body in order to move the one or more tabs between the retracted position and the extended position, each of the one or more extending blocks comprising an external surface configured to abut a portion of the internal surface of the respective tab, wherein the one or more extending blocks each have a rib slot comprising an opening in the external surface of the extending block, wherein generally parallel sides of the rib slot extend away from the external surface of the extending block and each meet a bottom surface of the rib slot, wherein a distance between the sides of the rib slot is uniform within the rib slot from the external surface of the extending block to the bottom surface, to surround a uniform width of the respective support rib;

wherein an angle formed by the portion of the internal surface of the respective tab that abuts the external surface of the respective block with respect to the path is incongruent with an angle formed by an internally facing surface of the support rib that faces the bottom surface of the respective rib slot with respect to the path.

* * * * *